United States Patent [19]

Lundquist et al.

[11] Patent Number: 5,059,167

[45] Date of Patent: Oct. 22, 1991

[54] RETROPERFUSION AND RETROINFUSION CONTROL APPARATUS, SYSTEM AND METHOD

[75] Inventors: Ingemar H. Lundquist, Pebble Beach; Zoltan Tarczy-Hornoch, Berkeley; Thomas J. Kardos, Laguna Beach, all of Calif.

[73] Assignee: Retroperfusion Systems, Inc., Costa Mesa, Calif.

[21] Appl. No.: 523,173

[22] Filed: May 14, 1990

Related U.S. Application Data

[63] Continuation of Ser. No. 120,591, Nov. 13, 1987, abandoned, which is a continuation-in-part of Ser. No. 56,401, May 29, 1987, Pat. No. 4,865,581.

[51] Int. Cl.⁵ .............................................. A61M 1/00
[52] U.S. Cl. .......................................... 600/17; 600/16
[58] Field of Search ................................... 600/16–18; 604/97–99, 67, 101

[56] References Cited

U.S. PATENT DOCUMENTS

| | | | |
|---|---|---|---|
| 3,505,987 | 4/1970 | Heilman | 600/18 |
| 3,698,381 | 10/1972 | Federico et al. | 600/17 |
| 3,720,199 | 3/1973 | Rishton et al. | 604/98 |
| 3,985,123 | 10/1976 | Herzlinger et al. | 600/17 |
| 4,046,137 | 9/1977 | Curless et al. | 600/17 |
| 4,116,589 | 9/1978 | Rishton | 600/18 |
| 4,334,180 | 6/1982 | Bramm et al. | 600/17 |
| 4,459,977 | 7/1984 | Pizon et al. | 600/17 |
| 4,648,384 | 3/1987 | Schmukler | 604/4 |
| 4,689,041 | 8/1987 | Corday et al. | 604/99 |
| 4,741,328 | 5/1988 | Gabbay | 604/99 |
| 4,794,910 | 1/1989 | Mushika | 600/18 |
| 4,796,606 | 1/1989 | Mushika | 600/18 |
| 4,832,005 | 3/1989 | Takamiya et al. | 600/18 |

Primary Examiner—Lee S. Cohen
Assistant Examiner—Kennedy J. Schaetzle
Attorney, Agent, or Firm—Flehr, Hohbach, Test, Albritton & Herbert

[57] ABSTRACT

Retroperfusion control apparatus for supplying arterial blood of a patient to the venous side of the patient's heart including a pump having an inlet and an outlet and a piston movable through a pump stroke for moving a liquid from the inlet to the outlet of the pump. A stepper motor is provided which drives the piston. Electronic circuitry is provided for driving the stepper motor and senses the presence of an R wave in a patient to operate the stepper motor in response to the sensed R wave.

16 Claims, 11 Drawing Sheets

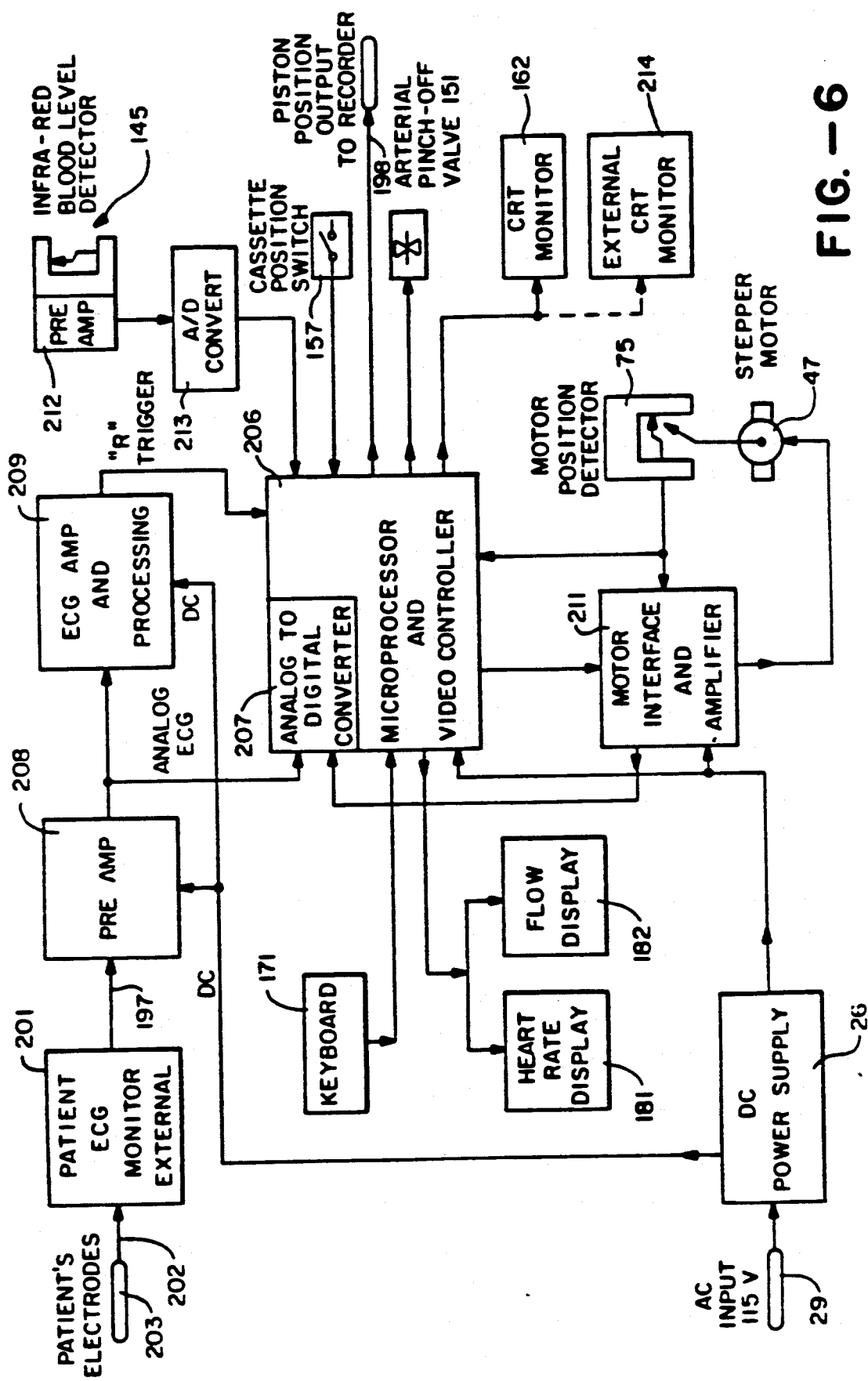
FIG.—6

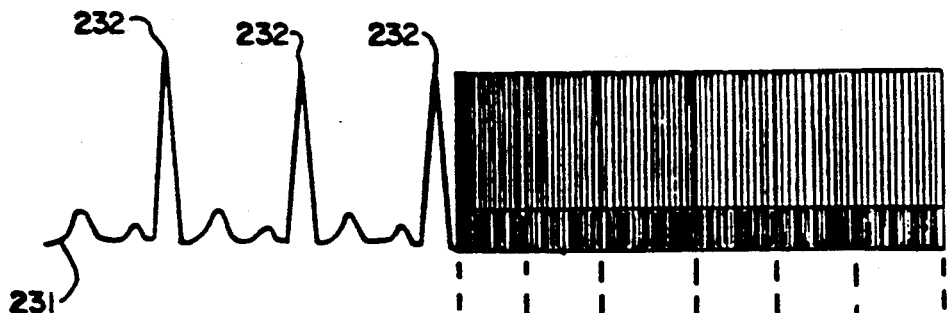
FIG.—7A
FIG.—7B
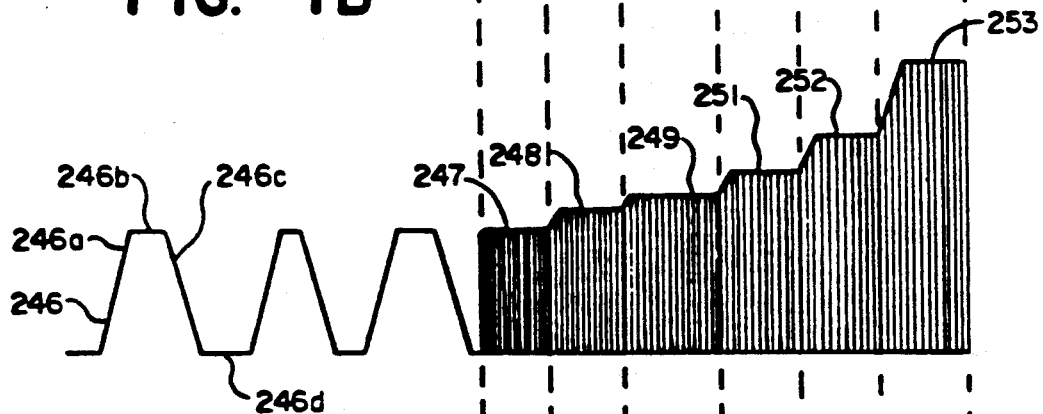
FIG.—7C
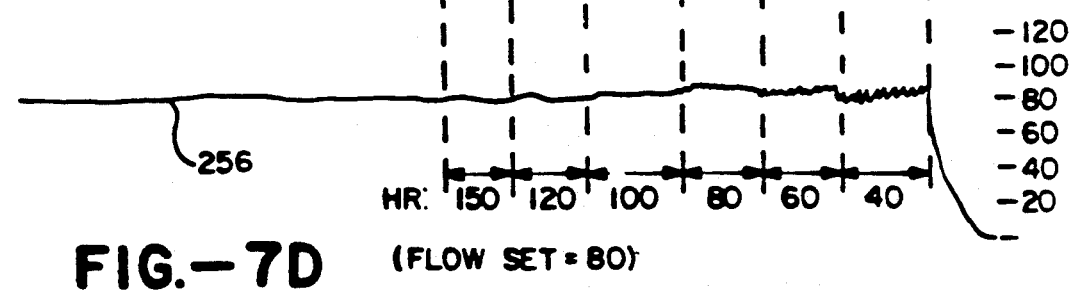
FIG.—7D  (FLOW SET = 80)

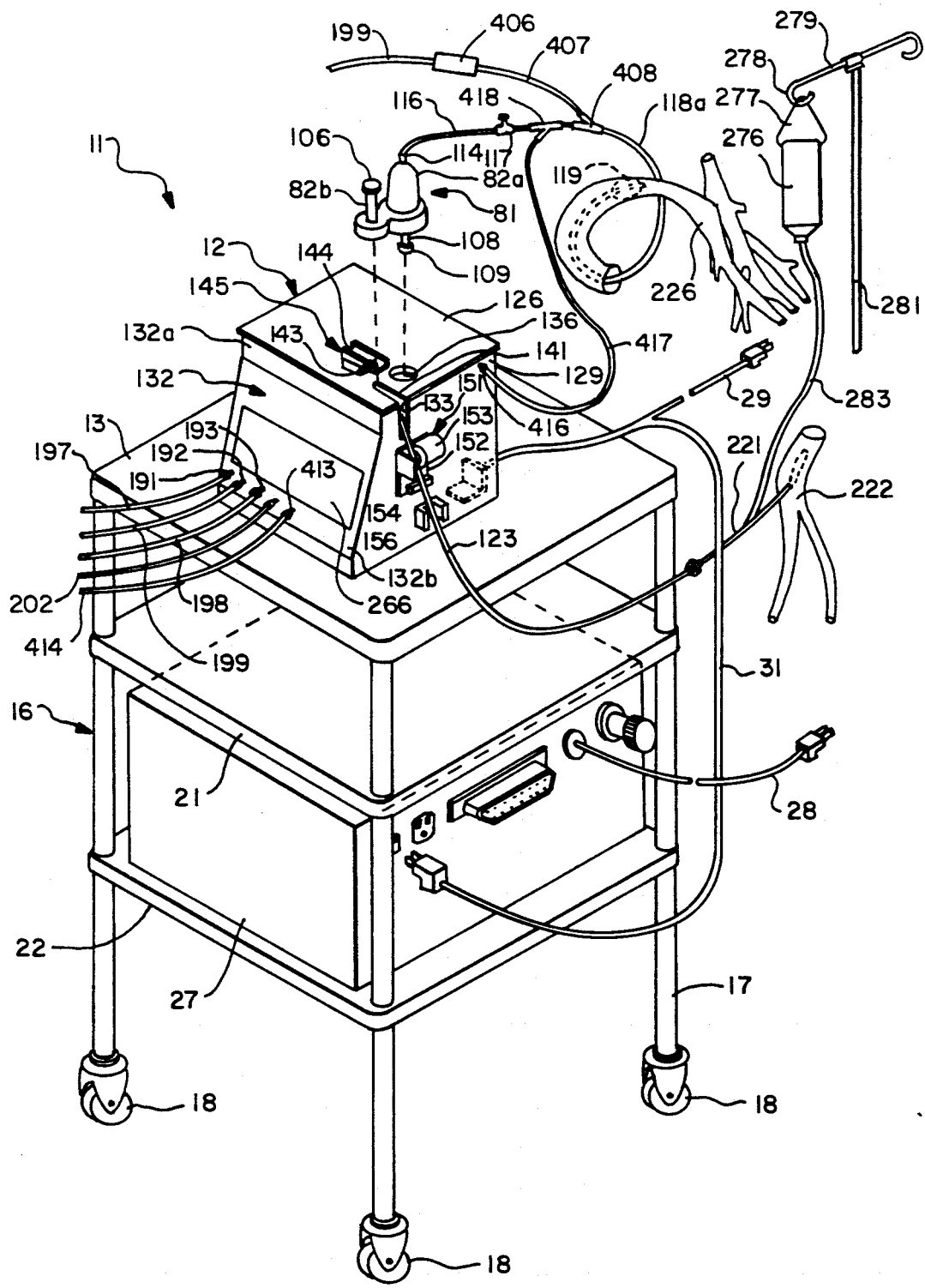
FIG.—8

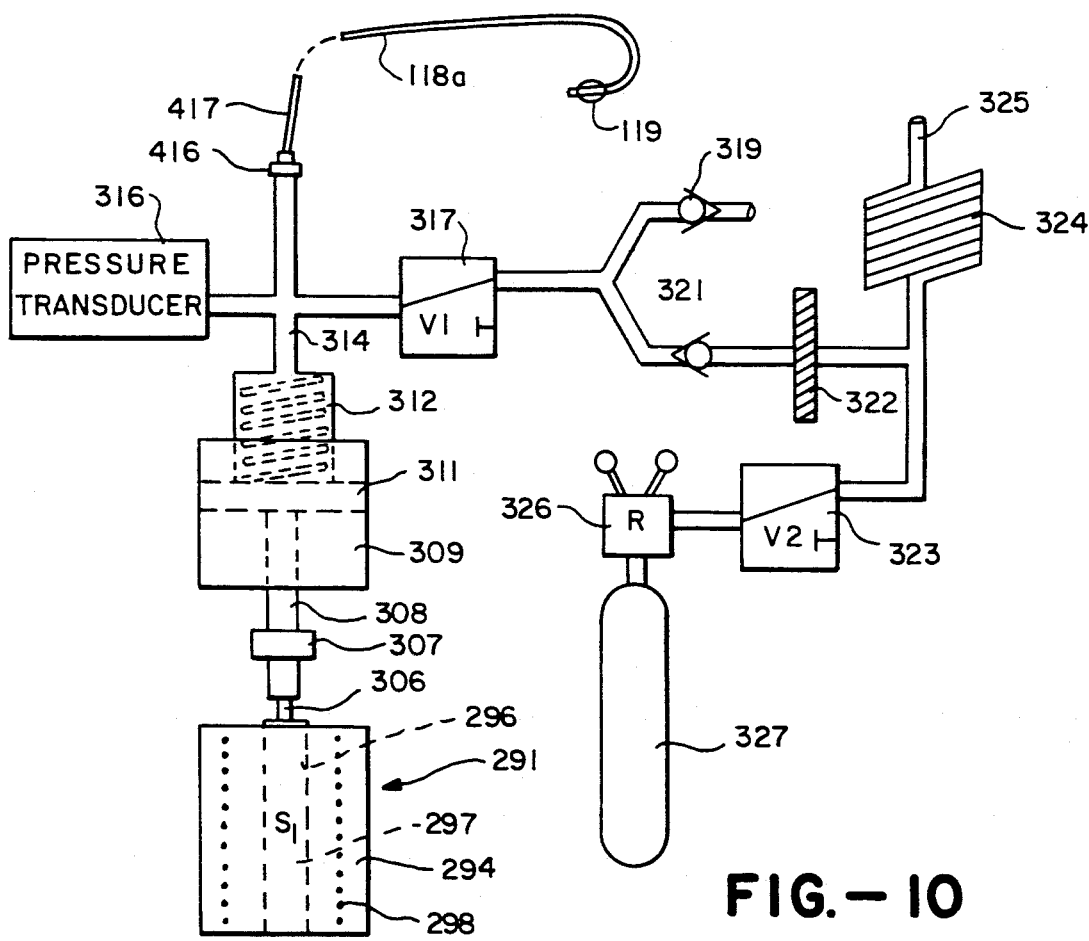
FIG.—10
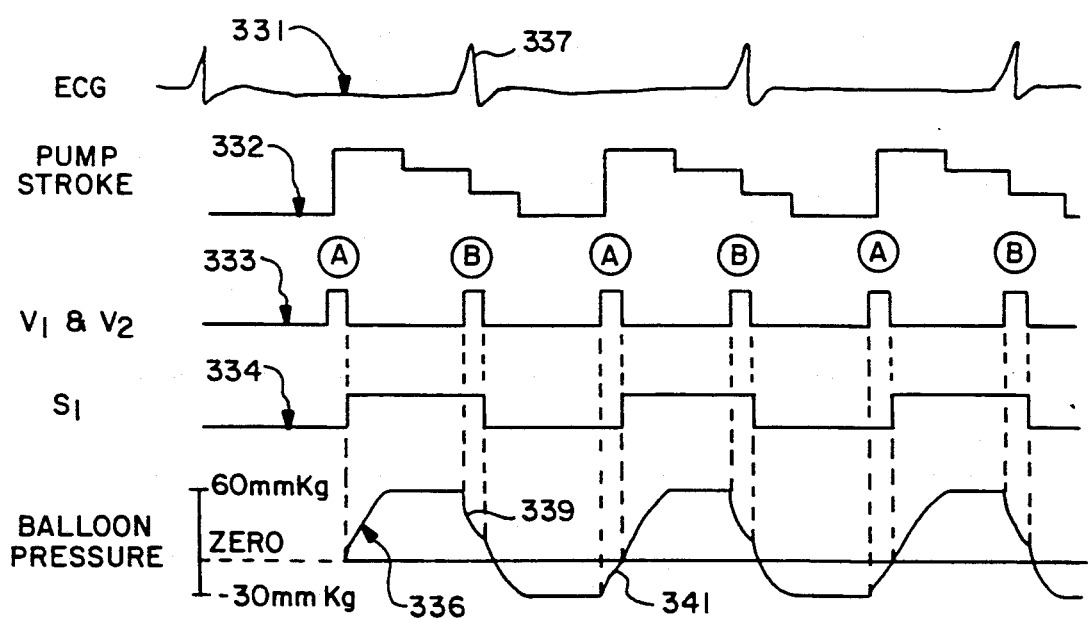
FIG.—11

RETROPERFUSION AND RETROINFUSION CONTROL APPARATUS, SYSTEM AND METHOD

This is a continuation of application Ser. No. 120,591, filed Nov. 13, 1987, now abandoned, which is a continuation-in-part of Ser. No. 056,401, filed May 29, 1987, now U.S. Pat. No. 4,865,581.

This invention relates to a retroperfusion, retroinfusion control apparatus, system and method.

Attempts have heretofore been made to perform synchronized diastolic coronary venous retroperfusion. Results are published in the Aug. 1985 issue of the *Journal of the American College of Cardiology*, Vol. 6, No. 2, pages 328-335 and in *Circulation*, Aug. 1986, Vol. 74, No. 2, pages 381-388. Both of these articles describe work which was done in connection with a synchronous retroperfusion system (USCI Model ECI). Such a system consists of a Hewlett Packard 78346A monitor for display of cardiac rhythm, arterial pressure and the pump signal. The monitor is a two-channel unit which is capable of monitoring and displaying the electrocardiogram and pressure or pump timing. Information from the monitor is fed and processed by the pump controller which operates a piston driven pump to maintain pump flow and pump timing through feedback circuits that compensate for variations in the patient's heart rhythm and rate. The piston driven pump is of the disposable type and is connected through tubing between the arterial blood supply and an auto-inflatable retroperfusion balloon catheter which is positioned in the great cardiac vein via the coronary sinus. As arterial blood is delivered through the coronary sinus catheter during diastole, this arterial blood inflates a balloon at the tip of the catheter. Inflation of the balloon seals the coronary sinus preventing leakage of arterial blood and permits a more effective retrograde delivery of arterial blood into the myocardium. On termination of retrograde catheter perfusion at or near end-diastole, the reverse stroke of the pump creates a back flow into and through the catheter which attempts to deflate the balloon. The amount of balloon deflation is heart rate and flow rate dependent. This allows retrograde coronary sinus drainage of venous blood from the myocardium into the right atrium during systole. Even though such work has been carried out in connection with retroperfusion, there is a need for a new and improved apparatus and system for carrying out such retroperfusion and an improved method for accomplishing the same. Essentially a retroperfusion control apparatus, system and method is disclosed in application Ser. No. 056,401 filed on May 29, 1987. In addition, it has been found that it is desirable to provide an apparatus, system and method which can be utilized for retroinfusion and which does not require the use of autoinflatable balloons. There is therefore a need for an improved apparatus and system which can be utilized for carrying out retroinfusion as well as retroperfusion.

In general, it is an object of the present invention to provide a retroperfusion and retroinfusion control apparatus, system and method which makes it possible to accomplish retroperfusion and retroinfusion in humans more proficiently.

Another object of the invention is to provide a retroperfusion and retroinfusion apparatus, system and method of the above character in which adjustable delivery rate by stroke length and timing of pumping is utilized which is synchronized to the heart's R-wave signals.

Another object of the invention is to provide a retroperfusion and retroinfusion control apparatus, system and method of the above character in which the pump cycle is always terminated at or before the beginning of a new R-wave.

Another object of the invention is to provide a retroperfusion and retroinfusion control apparatus, system and method which utilizes a microcomputer for monitoring the R-waves for initiating and terminating the pump cycle.

Another object of the invention is to provide a retroperfusion and retroinfusion control apparatus, system and method of the above character which can accommodate irregular heartbeats in the patient.

Another object of the invention is to provide a retroperfusion and retroinfusion control apparatus, system and method of the above character in which a computer controlled stepping motor is utilized for providing an adjustable delivery rate such as by adjustable pump stroke and adjustable stepping rate.

Another object of the invention is to provide a retroperfusion and retroinfusion control apparatus, system and method in which it is possible to specify delivery volume/time and/or delivery pressures.

Another object of the invention is to provide a retroperfusion and retroinfusion control apparatus, system and method of the above character in which the pumping can be controlled with great precision.

Another object of the invention is to provide a retroperfusion and retroinfusion control apparatus, system and method which utilizes a powered downstroke or rearward as well as powered upstroke or forward stroke.

Another object of the invention is to provide a retroperfusion and retroinfusion control apparatus, system and method in which an active precisely controlled vacuum stroke of the pump motion is provided to accentuate deflation of the blood inflated balloon.

Another object of the invention is to provide a retroperfusion and retroinfusion control apparatus, system and method in which the ECG signal from the patient is differentiated to find the maximum positive slope of the ECG waveform to provide an independent signal that an R wave is occurring or arterial pressure is differentiated to find a maximum negative slope to provide an independent signal that diastole is beginning.

Another object of the invention is to provide a retroperfusion and retroinfusion control apparatus, system and method in which it is possible to more precisely ascertain when the R wave is occurring.

Another object of the invention is to provide a retroperfusion and retroinfusion control apparatus, system and method in which a reversing action is utilized in the pump to facilitate deflation of the blood inflated balloon.

Another object of the invention is to provide a retroperfusion and retroinfusion control apparatus, system and method which utilizes a pinch-off valve for shutting off blood flow during non-pumping modes.

Another object of the invention is to provide a retroperfusion and retroinfusion control apparatus, system and method of the above character which utilizes a blood level sensor to detect blood supply problems such as an air leak or an occluded supply catheter or tubing.

Another object of the invention is to provide a retroperfusion and retroinfusion control apparatus, system and method of the above character which incorporates numerous safety features.

Another object of the invention is to provide a retroperfusion and retroinfusion control apparatus, system and method of the above character in which it is possible to deliver greater quantity of oxygenated blood to the area at risk even though the patient may have complex arrhythmias.

Another object of the invention is to provide a retroperfusion and retroinfusion control apparatus, system and method of the above character in which the timing can be varied independently of blood flow to allow optimal perfusion of the myocardium.

Another object of the invention is to provide a retroperfusion and retroinfusion control apparatus system and method of the above character in which the blood of the patient is utilized for autoinflating the balloon or alternatively, a fluid is introduced exterior of the patient's body for inflating the balloon.

Another object of the invention is to provide a retroperfusion and retroinfusion control apparatus system and method of the above character in which gas is utilized for inflation of the balloon.

Another object of the invention is to provide a retroperfusion and retroinfusion control, apparatus, system and method of the above character in which a central control console is utilized having an electroluminescent flat panel display.

Another object of the invention is to provide a retroperfusion and retroinfusion, control, apparatus, system and method of the above character in which the sinus pressure is utilized to automatically control the pumping of blood and/or the balloon inflation.

Another object of the invention is to provide a retroperfusion and retroinfusion control apparatus, system and method of the above character in which an electronically isolated ECG input capability is provided.

Another object of the invention is to provide a retroperfusion and retroinfusion control apparatus, system and method of the above character in which electronics is provided which makes it possible to connect ECG electrode pads directly to the patient.

Additional objects and features of the invention will appear from the following description in which the preferred embodiment is set forth in detail in conjunction with the accompanying drawings.

FIG. 6 is a block diagram of the electronics used on the system incorporating the present invention.

FIGS. 7A, 7B, 7C and 7D are strip chart recordings showing test results of the apparatus of the present invention at different heart beat rates.

FIG. 8 is an isometric view control apparatus and system similar to FIG. 1 but modified to incorporate additional improvements and in particular to incorporate the capability of performing retroinfusion and gas inflation of the balloon.

FIG. 10 is a schematic illustration of the portion of the apparatus utilized for inflating the balloon with a gas.

FIG. 11 is a chart showing a timing diagram for the gas inflation apparatus shown in FIG. 10.

Figure 1:
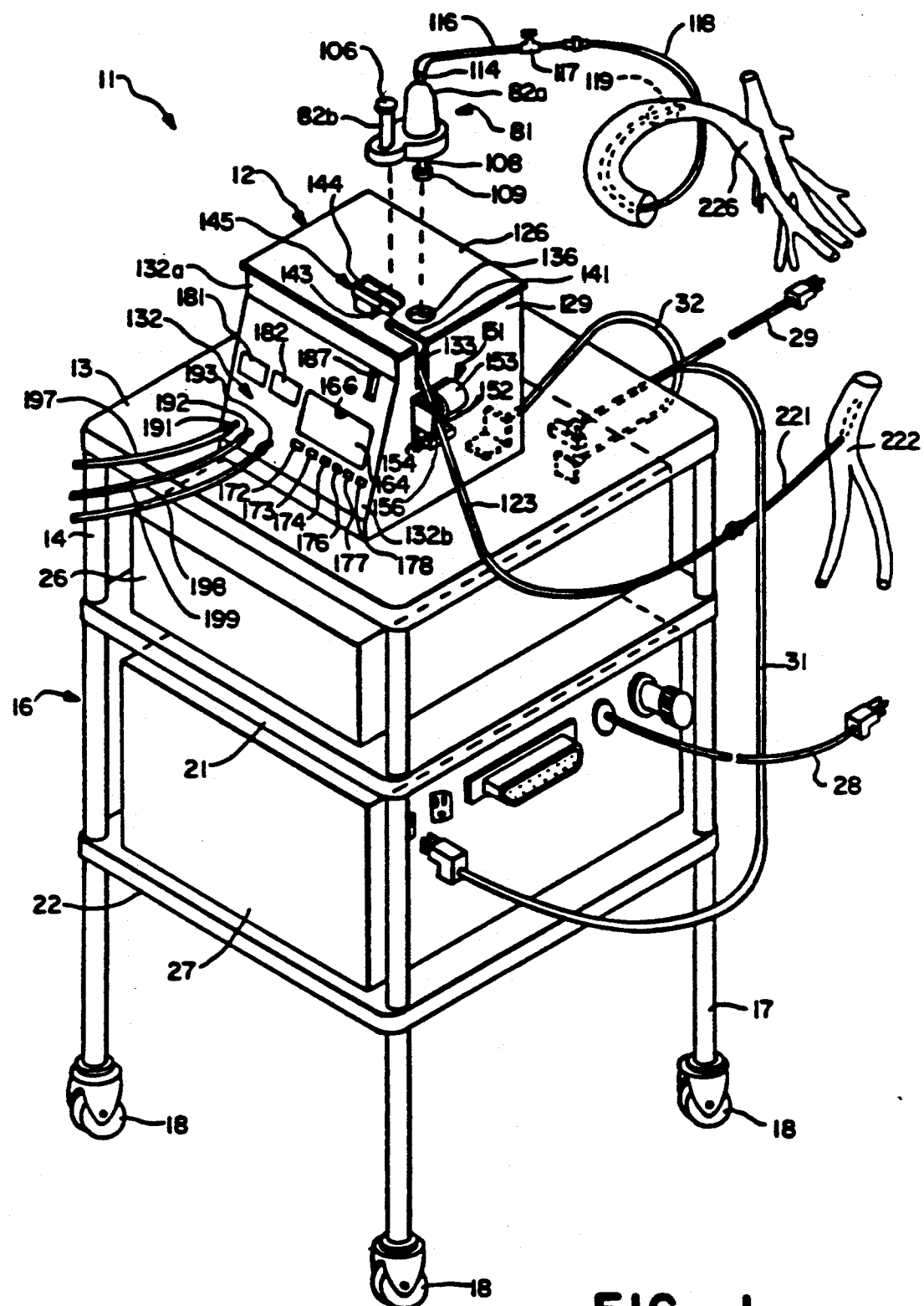
FIG. 1 is an isometric view of a retroperfusion control apparatus and system incorporating the present invention and showing the disposable pump about to be inserted into the same.

In general, the retroperfusion and retroinfusion control apparatus is comprised of a positive displacement pump having an inlet and an outlet, piston-like means for moving liquid from the inlet to the outlet, a stepper motor, means coupling the stepper motor to the piston-like means for causing operation of the piston-like means, electronic circuitry for driving the stepper motor, the electronic circuitry including means for sensing the R wave of a patient for operating the stepper motor, and for displaying the electrocardiogram, R wave, and pump stroke timing in relation to the above.

More in particular, the retroperfusion and retroinfusion control apparatus and system 11 consists of a pump console 12 which is supported on the top level 13 of an equipment dolly or stand 14. The equipment dolly or stand 14 is provided with a rectangular framework 16 which has four depending legs 17 having casters 18 mounted on the bottom extremities of the same. The equipment dolly or stand 14 is provided with an intermediate level shelf 21 and a lower level shelf 22 which are carried by the legs 17.

A power supply 26 for the pump console 12 is mounted upon the intermediate shelf 21. A backup power supply 27 of the battery type is mounted on the lower shelf 22. The backup power supply 27 is provided with a conventional electrical cord 28 which is adapted to be connected to a conventional source of ac, as for example, 110 volts 60 cycle ac. The power supply 26 is provided with a similar electrical cord 29 which also is adapted to be connected to either a conventional type ac outlet or the backup power supply 27. Another electrical cord or cable 31 is provided which interconnects the backup power supply 27 to the power supply 26. A cord 32 connects the power supply 26 to the pump console 12.

The pump console 12 is provided with an internal metal framework 36 which is divided into a pump drive compartment 37 a monitoring compartment 38 which is positioned below the pump drive compartment 37 and pc board compartments 39 and 41 which are mounted on the other side of the framework 36. The pump drive compartment 37 is provided with a support plate 46 which forms a part of the framework 36. A stepping motor 47 is mounted on the support plate 46 and is provided with an output shaft 48 that extends through the support plate 46. Another support plate 56 is provided which is mounted upon posts 57 carried by the support plate 46. A rack 61 is mounted for vertical reciprocation in a bracket or slide 62 which is mounted upon the support plate 56. A pinion 63 engages the rack 61 and is mounted upon a shaft 64 that is carried by a coupling 66 mounted upon the output shaft 48.

Yieldable spring means reduces the drive system compliance by preloading rack 61 in tension and consists of a spring 71 which has one end connected to a pin 72 which travels with the rack 61 and which has the other end connected to a pin 73 which is mounted upon the support plate 56. Motor position switch means 75 is provided for giving a timing signal when the rack 61 has reached its lowermost position and consists of infrared sensing means in the form of a light emitting diode 76 and a photosensor 77 carried by a bracket 78 mounted on the plate 46. A vane 79 mounted on the coupling 66 is adapted to pass between the diode 76 and the photosensor 77 to provide the timing signal.

Figure 5:
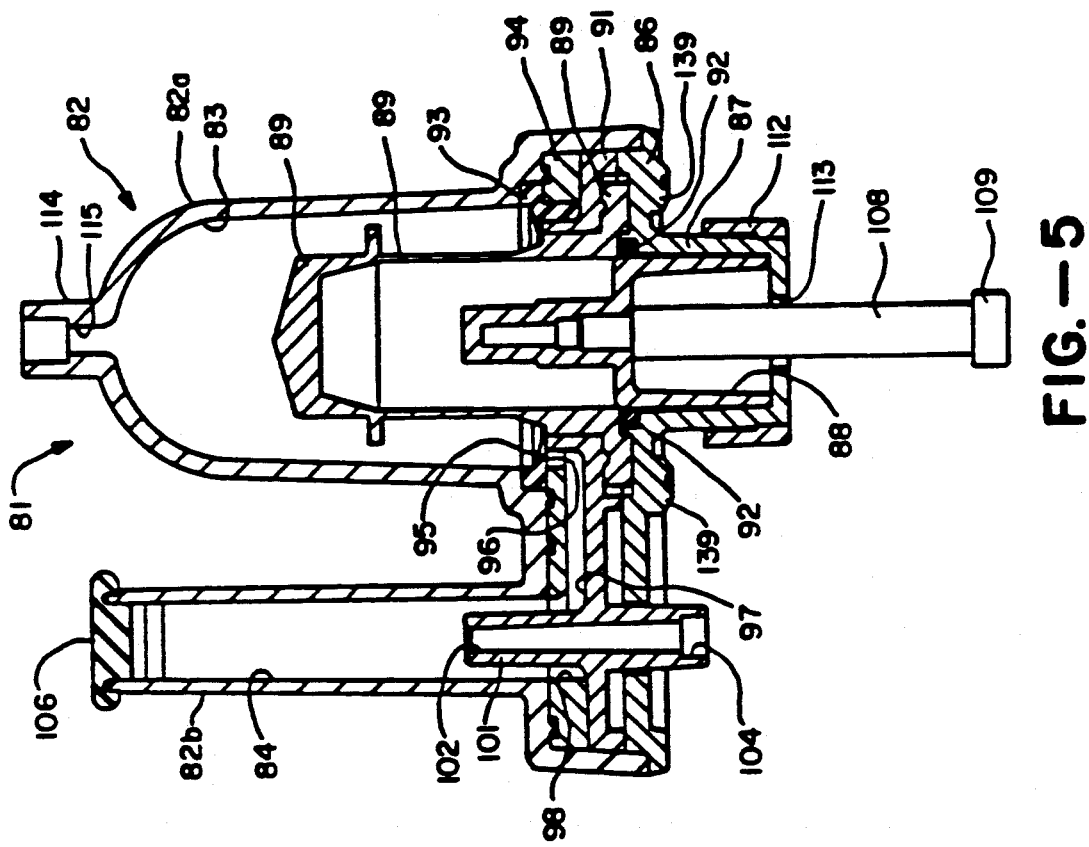
FIG. 5 is a side elevational view in cross section of the pump shown in FIG. 4.
Figure 4:
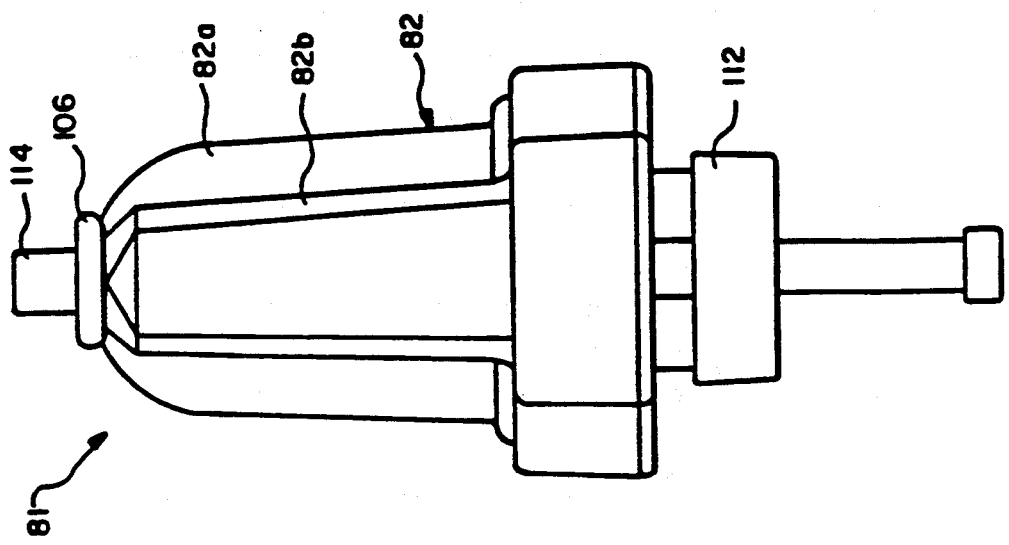
FIG. 4 is a front elevational view of a disposable pump incorporating the present invention.

A disposable pump cassette 81 adapted to be utilized with the pump console 12 is shown in FIGS. 4 and 5 and consists of a pump body 82 which is provided with two portions 82a and 82b in which portion 82a is dome-shaped and forms a pump chamber 83 and portion 82b is semi-cylindrical and forms a bubble chamber 84. A pump base 86 is secured to the lower extremity of the pump body 82 by suitable means such as ultrasonic welding. The pump base 86 is provided with a cylindrical depending open ended portion 87 which opens into the chamber 83. A piston 88 is mounted for reciprocatory movement within the cylindrical portion 87 and extends upwardly into the chamber 83. A boot 89 of a suitable material such as a silicon rubber is positioned over the piston 88 and has its lower outer margin secured between the pump base 86 and a boot retainer 91.

An O-ring 92 is disposed below the boot 89 and is in sealing engagement with the cylindrical surface of the piston 88 as shown particularly in FIG. 5. A seal member 93 of a suitable material such as silicone rubber is disposed in the pump chamber 83 and has its outer margin clamped between the pump body 82 and a retainer 94. An offset flapper valve member 95 as shown is provided with a tapered construction so that its thickness decreases progressively towards the inner margin of the same. The valve member 95 overlies a flow passage 96 which is in communication with a flow passage 97 that extends into a semi-annular flow passage 98 opening into the bubble chamber 84.

The boot retainer 91 is provided with a cylindrical upstanding portion 101 which opens into the interior of the bubble chamber 84. The cylindrical portion 101 is provided with a flow passage 102 which extends downwardly through the same and through the pump base 86 to inlet connection 104. A resealable membrane cap 106 formed of a suitable material such as rubber is mounted on top of the portion 82b of the pump body 82 and encloses the chamber 84. A plunger or lower piston rod 108 is provided which is secured to the piston 88 and depends downwardly therefrom. The piston rod 108 is provided with a head 109 which is adapted to seat within a recess 111 provided in the upper extremity of the rack 61. A retaining cap 112 having an opening 113 through which the piston rod 108 extends is secured to the lower extremity of the cylindrical portion 87. A protrusion 114 is provided on the upper extremity of the pump body 82 and is provided with a flow passage 115 therein which opens into the pump chamber 83.

In order that the pump cassette be disposable, it is desirable that the pump cassette be formed of inexpensive materials. With the exception of the boot 89, the seal and valve member 93, the O-ring 92 and the cap 106, all of the remaining parts can be formed of a suitable material, such as plastic. The use of clear plastic makes it possible to see into the pump chamber 83 and into the bubble chamber 84.

The protrusion or outlet 114 is sized so that a tubing 116 can be bonded to it. The tubing 116 is provided with a tee fitting 117 and is adapted to be connected to an auto-inflatable retroperfusion balloon catheter 118 of a conventional type which is introduced into the venous side of the heart during retroperfusion operations as hereinafter described. The catheter 118 is provided with an inflatable balloon 119. The tubing 123 is adapted to be connected to an arterial blood supply as hereinafter described.

The pump console 12 is provided with a top wall 126 which forms a part of the framework 36. It is also provided with a bottom wall 127, a rear wall 128, side walls 129 and 131 and a front wall 132. The front wall 132 is provided with an upper vertical portion 132a and lower inclined portion 132b. The compartment 124 opens to the exterior through a slot 133 in the side wall 129. The top wall 126 is provided with an opening 136 through which the lower extremity of the disposable pump cassette 81 can extend and in particular so that the retaining cap 112 can engage lips 137 which extend into the opening 136 at the time that the head 109 is slid into the recess 111. Yieldable means is provided for retaining the disposable pump cassette 81 in a predetermined position on the top wall 126 and includes a pair of spring urged detents 138 which are carried by the top wall 126 adjacent the opening 136 and which are adapted to engage dimples 139 provided on the bottom side of the pump base 86.

The top wall 126 is provided with another slot 141 which is adapted to receive the protrusion 104 and the tubing 123 carried thereby. As the pump cassette 81 is moved into place, the portion 82b of the pump body 82 forming the bubble chamber 84 is moved in between a pair of spaced apart members 143 which are mounted on a post 144 provided on the top plate or wall 126.

Infrared sensing means 145 is provided for sensing the level of liquid in the bubble chamber 84 and consists of a pair of light emitting diodes 146 and photodiodes 147 which are carried by the members 143. One light emitting diode 146 is provided on each of the members 143 and one photodiode 147 is provided on each of the members with the photodiodes facing the light emitting diodes. The photodiodes are provided to sense when the level of the blood within the chamber 84 drops below a predetermined level to stop the pumping action as hereinafter described.

A pinch off valve mechanism 151 for cutting off arterial blood flow through the tubing 123 is provided on the side wall 129 of the pump console 12 and consists of a bracket 152 which is secured to the side wall 129. An electrical solenoid 153 is mounted on the bracket and is adapted to operate a clamping jaw mechanism 154 provided on the bracket 152. The clamping jaw mechanism 154 is of a conventional type and is spring loaded into an open position and is provided with a slot 156 therebetween which the tube 123 can extend. When the solenoid 153 is energized, the slot 156 is closed to pinch off flow through the compliant tubing 123. As soon as the solenoid 153 is de-energized, arterial blood flow resumes through the tubing 123.

Figure 2:
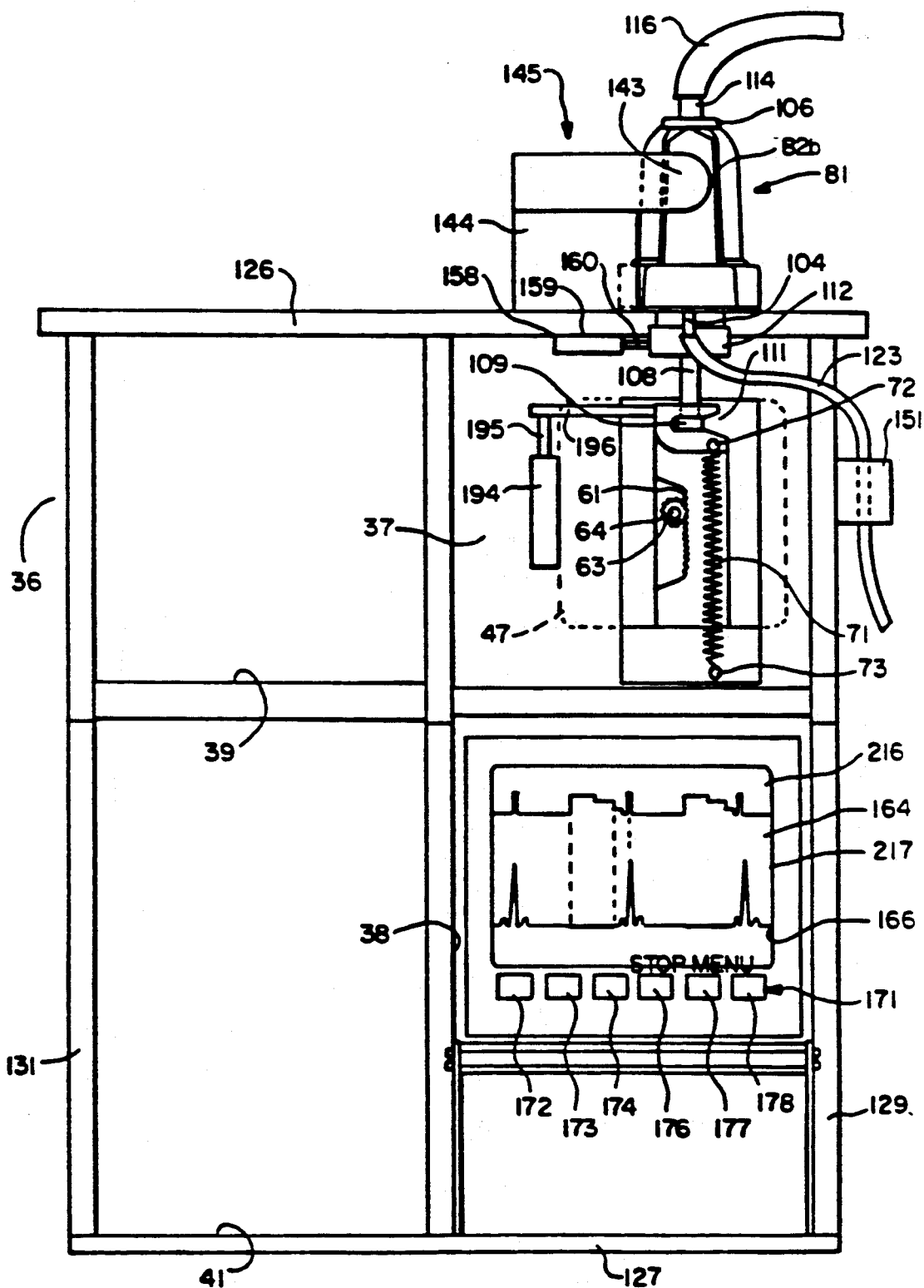
FIG. 2 is a front elevational view of the controller shown in FIG. 1.
Figure 3:
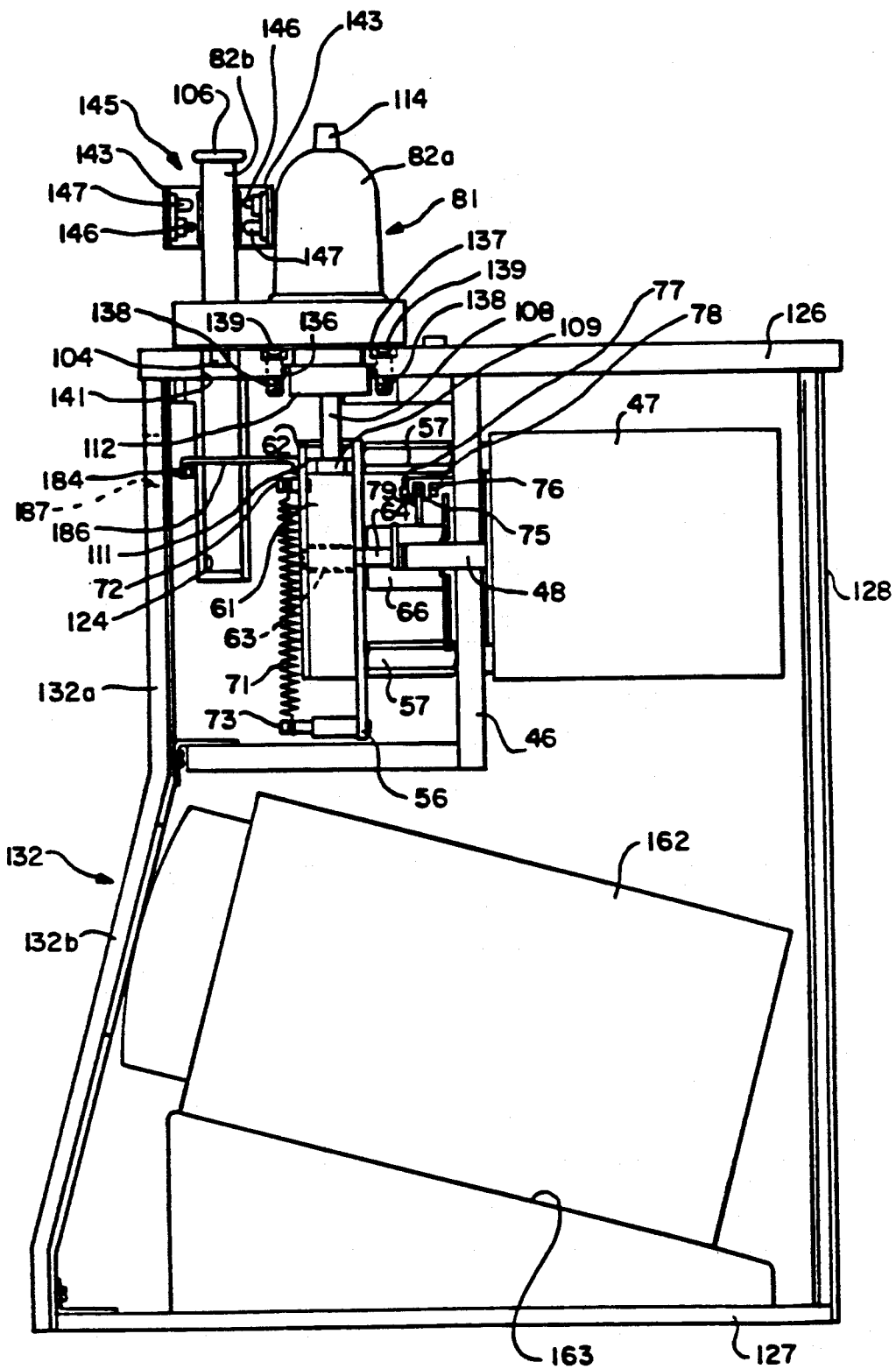
FIG. 3 is a side elevational view of the apparatus shown in FIG. 1.

Cassette position sensing means 158 is provided for ascertaining when the pump cassette 81 is properly positioned on the pump console 12. This sensing means 158 consists of a microswitch 159 mounted on the top plate 126 (see FIG. 2). It is provided with an operating arm 160 which engages the retaining cap 112 of the cassette 81.

A cathode ray tube 162 is mounted in the monitoring compartment 38 and is seated upon an inclined plane 163 mounted within the framework 36. The cathode ray tube 162 is provided with a screen 164 which is visible through an opening 166 provided in the front panel 132. A keyboard 171 is provided below the screen 164 and is provided with 6 push buttons 172, 173, 174, 176, 177 and 178.

Push button 172 is a spare. Push button 173 which carries an up-arrow function and push button 174 which carries a down-arrow function are utilized for increasing and decreasing the number of the various numerical parameters which are utilized for controlling operation of the pump cassette 81 as hereinafter described. The fourth key 176 is a start/stop key and controls the starting and stopping of the pump. The key 177 is the menu key and can be utilized for toggling between the ECG display screen and the numeric menu screen. The sixth key 178 is the line key. In addition to the main CRT screen 164 that can be viewed from the front panel 132, two three digit light emitting diode displays 181 and 182 are provided. Display 182 is for the flow rate setting for the apparatus and display 181 is for displaying the heart rate which is being sensed from the electrocardiogram.

Another display on the front panel shows the travel of the rack 61 and is comprised of a light emitting diode 184 supported on a bracket 186 mounted on the rack 61 so that it travels vertically with the rack. The travel of the light emitting diode 184 is visible through a slot 187 provided in the front panel 132.

Three connectors 191, 192 and 193 are provided in the lower left-hand side of the front panel 132. The connector 191 is used for receiving the electrocardiogram signal output which typically is a one volt peak-to-peak signal coming from an external ECG monitor. The connector 192 is utilized for providing the pump stroke signal which can be utilized in a strip chart recorder for externally recording the operation of the apparatus. The third connector 193 provides a piston position signal which can be utilized in a strip chart recorder for externally recording plunger 108 position. This piston position signal is supplied by a linear potentiometer 194 having a movable armature 195 connected to plunger piston 108 by an arm 196. Alternatively, the third connector 193 can be utilized as an input for measuring pressure, for example, pressures in the coronary sinus.

Conducting cords or cables 197, 198 and 199 (see FIG. 1) are connected to the connectors 191, 192 and 193 respectively.

As shown in the block diagram in FIG. 6 showing the electronics for the apparatus and system of the present invention, the cord or cable 197 is connected to an external patient ECG monitor 201. The patient ECG monitor 201 is of a conventional type and is provided with conventional leads 202 which are connected to electrodes 203 that are secured to the patient's body in appropriate locations in a conventional manner.

The pump console 12 contains numerous printed circuit boards which contain the circuitry which is shown in FIG. 6. Thus there is provided a microprocessor and video controller board 206 which incorporates an analog-to-digital converter 207. The output from the patient ECG monitor 201 is supplied through a pre amp 208 which supplies its output to the analog-to-digital convertor 207 and also to an ECG amplifier and processing circuitry 209. The circuitry 209 provides an "R" trigger signal to the microprocessor video controller 206. The DC power supply 26 is connected to various components of the circuitry as shown in FIG. 6 as well as to the microprocessor and video controller 206. A motor interface and amplifier board 211 is provided which is used for controlling the stepper motor 47. Various other components of the pump console 12 are interconnected to the microprocessor video controller 206 as shown. These components include the keyboard 171 as well as the heart rate display 181 and the flow display 182. The motor position detector or switch means 75 associated with the stepper motor 47 is connected to the microprocessor and video controller 206 as well as to the motor interface and amplifier board 211. The infrared blood level detector 145 is connected through a preamplifier circuit 212 through an A/D converter circuit 213 to the microprocessor 206. The cassette position sensing switch 158, the arterial pinch off valve assembly 151 and the CRT monitor 162 are also connected to the microprocessor and video controller 206. The microprocessor 206 supplies an output to the connector 192 which can be connected to a strip chart recorder. If desired, as shown in FIG. 6, an additional external CRT monitor 214 can be utilized.

Operation and use of the retroperfusion apparatus and system in performing the method of the present invention may now be briefly described as follows. Let it be assumed that a patient has been identified in which it is desired to utilize a retroperfusion procedure. The equipment dolly or stand 14 is brought to the patient or conversely, the patient is brought to the equipment dolly where it is located. The cord 28 or 31 is connected into an appropriate power outlet in the hospital. The operator then observes the position of the rack 61 by noting the location of the small light emitting diode 184 which is viewable through the slot 187 provided on the front panel 132. This diode 184 should be at the bottom or home position. If it is not in the home position, the plunger 108 should be shifted in the cassette 81 so that it is in an appropriate position so that it can be inserted into the pump console 12. The pump cassette 81 can then be positioned so that the retaining cap 112 enters the opening 136 so that the head 109 carried by the piston plunger 108 can enter the slot or recess 111 provided at the top of the rack 61. At the same time this is occurring, the bubble chamber 84 is introduced into the infrared level detector 145. The on/off switch (not shown) for the power supply 26 can be operated to supply power to the control pump console 12. The screen 164 of the CRT monitor 162 should then be viewed to see whether or not the top trace 216 on the screen is a straight line. This trace 216 represents the pump stroke when the pump is being operated.

The cable 197 is then connected to the patient ECG monitor 201 and the ECG electrodes 203 are attached to the patient. The R wave signal on the video monitor 162 is then observed by observing the lower trace 217 on the screen 164 of the video monitor. The rate of rise of the R wave should always be greater than that of the T wave. Appropriate selection of ECG leads can be made on the patient to adjust the quality of the ECG signal. The cable 199 can then be connected to the strip chart recorder for recording the pump stroke cycle trace.

With an empty pump cassette in place, the start button 176 on the keyboard 171 can be pressed which will cause operation of the stepper motor 47 to cause operation of the rack to operate the plunger 108 of the cassette. Unless the preamp 212 blood level sensor 145 senses an appropriate blood level, only one pump stroke is taken and the pump stops, indicating an alarm condition.

The pump console 12 may now be set to the desired parameters. For example, an initial flow rate of 100 milliliters per minute per EKG can be set by pressing the menu button 177 to cause the menu screen to be displayed. The up and down keys 173 and 174 can then be utilized to select the correct value for flow. As soon as these values have been set the menu button 177 can be again pressed to enter the new value and execute the flow adjustment. The screen will again display the ECG signal and the pump stroke trace.

Utilizing conventional aseptic techniques, a conventional supply catheter 221 can be placed in the femoral artery 222 of the patient and connected to the tubing 123 to obtain a supply of arterial blood. The inflatable retroperfusion balloon catheter 118 is placed in the great cardiac vein 226 approximately 2 to 3 centimeters proximal to the anterior interventricular vein via the coronary sinus. Proper placement of the catheter 118 is confirmed under fluoroscopy by observing the free flow of a radiopaque solution around the catheter in the atrium during systole. A disposable pressure transducer (not shown) can be secured to the proximal end of the retroperfusion catheter's pressure lumen if it is so equipped, and can be connected to the cabling 198 which is connected to the pressure connector 193 provided on the front panel 132.

A sterile pump cassette 81 is placed on the pump console 12. The apparatus is then primed with a sterile heparinized saline solution. Any air bubbles which appear in the apparatus are removed by using a syringe to penetrate the cap 106 and withdrawing air from the bubble chamber 84. In order to ensure that all air is withdrawn from the apparatus, a syringe can also be utilized to draw blood back through the outlet tubing 116 and retroperfusion catheter into the injection site 117a to ensure that all air has been removed.

As soon as this has been accomplished, the pump can be placed in operation. As arterial blood is delivered through the coronary sinus catheter during diastole, the blood automatically inflates the balloon at the end of the auto-inflatable retroperfusion balloon catheter 118. This retards the efflux of blood from the regional coronary veins and permits effective retrograde delivery of arterial blood to the myocardium of the heart. Termination of the retrograde catheter perfusion at end of diastole, automatically deflates the balloon and permits antegrade coronary sinus drainage of venous blood from the myocardium into the right atrium during systole.

More specifically, the operation of the apparatus and in particular, the circuitry which is shown in FIG. 6 may now be described. The one volt peak-to-peak signal which is supplied from the external ECG monitor 201 has been prefiltered to approximately 150 hertz high frequency rolloff. A signal is supplied to the preamplifier 208 which accomplishes additional filtering and also supplies a signal to the A/D converter 207 connected to the microprocessor 206. A signal is also supplied from the preamp 208 to the ECG amplifier and processing circuitry 209 which is utilized to ascertain location of the R wave peak. This is accomplished by taking the electronic derivative of the signal to find the maximum slope in the wave form. This information is supplied as a signal on the R trigger circuit to the microprocessor 206. The microprocessor 206 has the capability of correlating the pattern which is generated by the A/D converter 207 based upon the ECG monitor and compares it with an independently generated R trigger circuit signal being supplied by the ECG amplifier and processing circuitry 209 to ascertain whether or not there is an agreement that an R wave has been detected which can be utilized for triggering the operation of the stepper motor 47.

The output of the microprocessor video controller 206 feeds signals to the stepper motor 47 that are phased in relationship to the stepper motor to create approximately 500 steps per inch of operation of the motor in forward and then in reverse and causing a resultant travel of the piston 88 in the pump cassette 81 between the upper and lower limits of movement for the piston 88. These steps of the stepper motor, and the rate at which these steps are taken, are controlled by the microprocessor 206 utilizing a lookup table and are based upon the heart rate input that is sensed by the ECG monitor 201 and the delivery setting which has been inserted by the physician into the pump console 12 by operation of the menu key 177 and the up and down keys 173 and 174 as hereinbefore described. In this manner, the microprocessor 206 determines precisely the upstroke time and speed as well as the pause time and the downstroke time and speed. The microprocessor 206 is capable of assimilating arrhythmias and abnormal ECG events. Typically the microprocessor 206 initiates the pump cycle at approximately 45% and terminates at 95% of the R to R period if the heartbeat is steady. The desired steadiness can be defined, e.g., no more than 10% change during the past eight heartbeats. If the rate is changing more rapidly, the pump is started later depending upon the rate of change to avoid premature pumping and straining of the heart. The pump cycle is always terminated at the beginning of a new R wave. After a very irregular beat the pump skips a pump cycle until the heartbeat stabilizes, all under the control of an algorithm.

As hereinbefore explained there are three feedbacks to the microprocessor from the stepper motor 47, from the pump cassette 81, and from the infra-red blood level detector 145. The first is the bottom of stroke indication from the motor position detector 75. The second input to the microprocessor 206 is the cassette position switch 158 which informs the microprocessor whether or not the cassette is actually connected to the stepper motor rack 61. Thus, if the cassette is improperly placed, the microprocessor 206 will stop the pumping operation. Information is also supplied from the infrared blood level detector 145 to the microprocessor 206 and causes the microprocessor 206 to shut down the pumping action when air bubbles are sensed in the blood or when the blood level within the bubble chamber 84 falls below the level of either of the infrared sensors of the blood level detectors 145.

The microprocessor 206 has been programmed so that the pump stroke will start at 45% of the R to R interval (the R period) and terminates at approximately 95% of the R to R interval. In programming this pumping operation, it has been found it is desirable to program the microprocessor 206 so that signals to the stepper motor 47 are entered twice as fast on the upstroke so as to leave approximately one half of the time allotted for the upstroke for a pause time after which the downstroke is commenced. The downstroke is accelerated in order to cause better deflation of the auto inflatable balloon 119 at the end of the catheter 118 and also to more quickly reduce the pressure from the coronary sinus caused by the pump stroke.

Such a flow pattern is shown in the traces shown in FIG. 7. The traces show that pumping into the coronary sinus actually begins at the end of systole or in other words at the end of the arterial pressure wave. Utilizing a pause between the upstroke and downstroke, the slope of the rise of flow is much steeper and achieves peak flow much earlier in the R to R cycle which makes it possible to achieve peak pressure in the coronary sinus earlier in the R to R cycle. This helps to prevent or avoid the generation of overpressures or collisions between the pressure due to flow caused by the pump and the pressure wave due to arterial pressure of the next systole. Thus it can be seen that this helps to avoid possible hemorrhaging in the heart. A downward or receiving portion of the flow occurs prior to the occurrence of the next R wave, thus pressure is removed more rapidly from the coronary sinus.

With such use of a pause phase, the same amount of blood can be delivered between the R to R peak but is delivered more rapidly and more appropriately in the diastolic time window. In addition the pressure is removed more rapidly to prevent any possible collision from the systolic arterial pressure wave. By adding the pause at the end of the upstroke, the pressure generated completely depletes and translates into maximum blood flow. The downstroke does not occur until after this pressure has been completely dissipated through the catheter and maximum flow has been expelled through the catheter. As the downstroke occurs, a greater negative pressure is created than would be the case without a pause. This greater negative pressure facilitates collapse of the balloon 119 of the auto-inflatable balloon catheter 118.

Thus it can be seen there are two effects from such a procedure. One is to deliver the pressure wave and the flow earlier in the R to R cycle and the other is to allow greater flow through the catheter by allowing the buildup of pressure to deplete itself and translate into greater blood flow with a subsequent improved collapse of the balloon.

In FIGS. 7A, 7B, 7C and 7D, there are shown four strip chart recordings which show the response of the pump 81 in response to heart rate variation. In achieving the data which is shown in FIGS. 7A, 7B, 7C and 7D, a retroperfusion apparatus and system of the present invention was utilized with the pinch valve assembly 151 being utilized for controlling the arterial blood flow. A patient ECG simulator was utilized to provide a normal rhythm. A conventional flow meter and a strip chart recorder were utilized. A saline solution was placed in a bag at 6 feet in elevation to simulate arterial pressure. A 7 French catheter with a 5 millimeter balloon was utilized. The catheter tip was introduced into a graduated cylinder so that the amount of saline solution which was pumped could be measured. In carrying out the tests, a calibration was performed for 0 to 100 milliliters per minute flow to calibrate the strip chart versus the graduated cylinder. In each of the flow settings of 20 to 120 milliliters per minute at 20 milliliter increments, the delivered mean flow was recorded on the strip chart recorder at heart rate settings of 60, 80, 100, 120 and 150 beats per minute. Recordings were made at both slow and fast recording speeds with each setting as shown in FIGS. 7A, 7B, 7C and 7D. After the calibration had been completed, the flow was set at 80 milliliters per minute and the heart rate was varied through 40, 60, 80, 100, 120 and 150 beats per minute at a fast strip chart speed and then varied through 150, 120, 100, 80, 60 and 40 beats per minute at slow speed for compressed recording. The results of the tests are shown in the traces in 7A, 7B, 7C and 7D.

The trace 231 is FIG. 7A, shows the electrocardiogram with the R peaks 232 as they are changed from a rate of 150 beats per minute to 120, 100, 80, 60, and 40 beats per minute. The phasic timing of the pump stroke is shown by the trace 236 in FIG. 7B. The highest level 237 of the trace indicates the upstroke time. The next lower level 238 indicates the duration of time that is occupied by the pause state where the pump piston is at its highest position and is held there for a predetermined period of time. The next level 239 indicates the time taken for the downstroke. The lowest level 241 indicates the pause or waiting time before the next trigger signal arrives to start the upstroke.

The trace 246 which is shown in FIG. 7C shows the actual pump piston position with respect to time. The movement of the piston during the upstroke is indicated by the upwardly sloped portion 246a of the trace 246. The pause for the piston at the upper limit of its travel is indicated by the flat portion 246b and the downwardly inclined slope portion 246c indicates the downward stroke of the piston. The flat portion 246d represents the pause before the next upstroke of the piston is started.

The trace 251 which is shown in FIG. 7D shows the time-averaged mean flow output from the pump through a calibrated flow meter and shows that a substantially constant output flow as, for example, 80 milliliters per minute for which the pump console 12 was set is achieved even though the beats per minute change radically. The trace in FIG. 7C show how this was accomplished. As the beats per minute decreases, as for example, 150 for the initial pump stroke as shown by the level portion 246b, which is represented by the level 247 for 150 beats per minute. As the heart rate decreases, a larger volume of blood must be pumped with each stroke and therefore the stroke length is increased as represented by level 248 for 120 beats per minute, level 249 for 100 beats per minute, level 251 for 80 beats per minute, level 252 for 60 beats per minute and level 253 for 40 beats per minute. The trace 256 in FIG. 7D shows that the output of the pump remains substantially constant through the entire operating range from 150 to 40 beats per minute. Thus it can be seen that the microprocessor 206 senses the change of rate of the heart beats and adjusts the upstroke time, the upstroke speed, the pause time and the downstroke time so that with the reduced number of strokes per minute increased volume is produced by the pump each time a stroke is made so that the resultant mean flow from the retroperfusion apparatus is substantially constant.

It has been found that once the system has been primed, there is no accumulation of air within the system because the system is sealed.

From the foregoing, it can be seen that there has been provided a retroperfusion apparatus system and method which has many advantages. The microprocessor controlled stepper motor drive provides a positive control over the pump stroke and provides a powered upstroke and a powered downstroke by forward and reverse motion of the stepper motor. The precisely controlled powered downstroke contributes to the balloon deflation. The microprocessor control which is utilized makes it possible to precisely detect the R waves by ascertaining the maximum positive slope within the ECG waveform and supplies a signal which is correlated with software in the microprocessor to ascertain whether in fact an R peak has occurred to therefore make possible a more positive and precise identification of the R wave. A direct coupling is provided between the stepper motor and the piston of the pump which direct coupling is obtained by the use of a rack and pinion.

Numerous safety features have been provided in the apparatus and system. In addition, the pinch-off valve in the arterial line clamps off the arterial line when the system is stopped or a fault alarm or condition occurs. This prevents flow through of the arterial blood. Thus, it can be seen that the pinch-off valve prevents passive flow through of arterial blood under arterial pressure through the system from the arterial side to the venous side. If the pinch-off valve were not present, it would be possible for such passive arterial blood flow to be as much as 30 milliliters per minute which could eventually fill the auto inflatable balloon and occlude the sinus for egress of blood which could have very deleterious effects on the patient.

Another embodiment of the retroperfusion and retroinfusion apparatus and system is shown in FIGS. 8–15 and is particularly adapted to perform retroinfusion as well as retroperfusion and which is adapted to be utilized with a gas inflated balloon which is inflated from a gas source external of the body, rather than being auto-inflated with the patient's blood.

Figure 9:
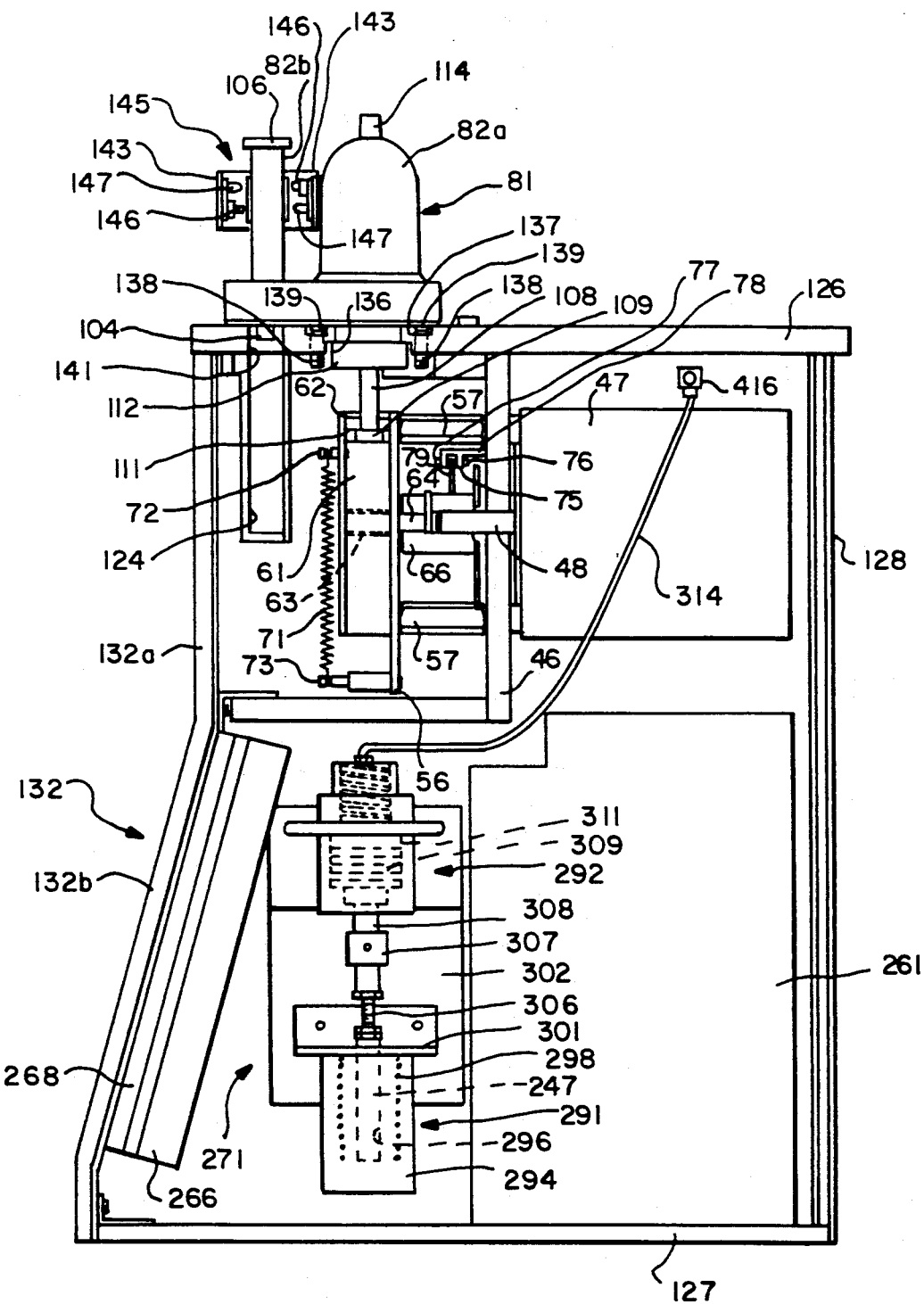
FIG. 9 is a side elevational view of the apparatus shown in FIG. 8.

As can be seen from the apparatus shown in FIGS. 8 and 9, major portions of the apparatus remain the same as shown in the previous embodiment of the invention. However, certain changes have been made. For example, the CRT display as represented by the cathode ray tube 162 has been removed and the space which was utilized by the same has been used to incorporate a power supply 261 which takes the place of the separate power supply 26 shown in FIG. 1. This makes the pump console 12 self-contained except for the use of the backup power supply 27. Also in place of the CRT, an electroluminescent flat panel display 266 has been provided. The flat panel display 266 can be of any suitable type, such as one produced by Finlux Corporation of Finland, having by way of example 512×256 dot resolution. In addition, the six pad keyboard comprised of the switches 172, 173, 174, 176, 177 and 178 have been eliminated and a touch panel 268 has been provided which has been laminated directly over the display panel 267. This touch panel 268 is substantially transparent and can be operated by touching it with a finger or pen or some other object, in particular places on the touch panel to cause it to serve as a keyboard input. As also shown in FIG. 9, a gas inflation mechanism or apparatus for balloon inflation as hereinafter described is incorporated in the space previously occupied by the CRT and is disposed behind the electroluminescent display panel 266 and in the front of the power supply 261.

In order to provide retroinfusion capability for the apparatus and system, a container such as a flexible bag or a bottle 276 is provided which can carry a diluent or a drug liquid within the container 276. The container or reservoir 276 can be suspended in a conventional manner such as by utilizing a strap 277 carried by the container 276 and secured to a hook 278 carried by a support member 279 mounted upon a stand 281. Suitable conventional means (not shown) can be utilized for controlling the flow of the liquid contained within the container 276 and for supplying the same into a tube 283 which can be connected in a suitable manner to the tube 221 to permit the drug or diluent to be supplied in the blood for the coronary sinus in an ECG synchronized or a non-synchronized manner. Thus the drug or diluent is introduced into the pumping circuit by connecting the pump inlet line previously attached to the arterial catheter to the reservoir 276 containing the drug or diluent retroinfusate. For the non-synchronized mode, the pump mechanism is operated at a high frequency (as for example, 300 cycles per minute) with each cycle providing a small stroke (such as less than 1 cc) such that the result of pulsatile flow approximates a continuous flow. Alternatively for low flows a slow stroke over a long time duration is provided while the pinch valve 153 is closed, with a fast filling stroke while the pinch valve 153 is open. These allow utilization of a pulsatile type pumping cassette for generating near continuous flow. In the synchronous approach, the flow is controlled in conjunction with the sensed sinus pressure and independently of the balloon inflation/deflation timing.

In the present embodiment, rather than using an auto-inflatable balloon, gas inflation means is provided for inflating and deflating the retroperfusion catheter balloon 119 in synchronism with each pump stroke or alternatively, in response to sensed sinus pressure. This gas inflation mechanism 271 is shown in FIG. 9 and schematically in FIG. 10. As shown therein, it consists of a solenoid assembly 291 having a cylindrical core 294 which is provided with a centrally disposed bore 296. A plunger 297 is slidably mounted in the bore. A winding 298 is provided on the core 294. The solenoid assembly 291 is mounted on a bracket 301 which is secured to a plate 302 mounted within the control console. The plunger 297 is provided with a shaft 306 which is connected by a coupling 307 to a shaft 308 carried by the bellows assembly 292. The shaft 308 is a part of the bellows assembly 292. The bellows assembly 292 consists of a collapsible cylindrical member 309 in the form of a collapsible bellows of a suitable type such as those supplied by Bellofram. Means is provided for yieldably urging the piston 311 in a direction towards its home position and consists of a spring 312 carried within a housing 313 and having one end of the spring engaging the piston 311 to return the bellows to its normal or at home position. As shown in FIG. 10, this tubing 314 is connected to a pressure transducer 316. It is also connected into the catheter 118 and also to the input of the solenoid operated valve V1 also identified as valve 317. The outlet from the valve 317 is connected to a tube 318 which is connected to two one-way check valves 319 and 321. The check valve 319 is open to ambient whereas the check valve 321 is connected through a filter 322. The filter 322 is connected to the outlet of a solenoid operated valve V2, also identified as valve 323. The outlet of the valve 323 is also connected to a linear plenum 324 which is open to ambient or to the atmosphere. The inlet to the valve 323 is connected to a one-stage regulator 326 mounted upon a tank or container 327 containing a suitable gas as, for example, carbon dioxide or helium. The valve V2 supplies gas to the linear plenum 324 which feeds substantially zero pressure gas to the bellows 309 through the filter 322 through the check valve 321 through the valve V1 through the tubing 314 through the spring and into the bellows 309.

A stroke of approximately ⅛inch is utilized for the solenoid 291 to ensure there is adequate force applied by the solenoid 291 to the bellows 309. However, it should be appreciated that if desired a longer stroke can be utilized. When the solenoid assembly 291 is energized, the piston 311 of the bellows 309 is moved to create a positive pressure against the yieldable force of the spring 312 forcing gas into the catheter 118 and into the balloon 119. As soon as the solenoid assembly 291 is deenergized, the piston 311 is returned to its home position by the spring 312 which causes deflation of the balloon 119.

The solenoid operated valves V1 and V2 ensure that proper positive and negative pressures are provided within the bellows-balloon pneumatic circuit connected to the balloon 119. The solenoid valves V1 and V2 are pulsed with pulses having a width ranging from 10 to 20 milliseconds at the beginning of each inflation and deflation cycle for the balloon 119. The symbols for the valves V1 and V2 as shown in FIG. 10 indicate that both of the valves have two positions, in one position they are open, in the other position they are closed. For both valves when the 10 to 20 millisecond pulses are supplied they are set to be in the open position. When the pulses are not supplied, the valves are in the closed position.

The one-stage regulator 326 can provide a desired pressure between 1 and 50 psi. The linear plenum 324 is in the form of a long coiled tube which serves as a linear path for the gas so that whatever gas comes from the pressurized cylinder 327 will go through and exit to ambient to ensure that ambient air will not be drawn into the pneumatic circuit. The point at which the filter 322 meets the linear plenum 324 is a substantially zero pressure junction and is the point where gas from the cylinder 327 is transferred through the one-way valve 321 into the bellows balloon pneumatic circuit. The transfer of gas into the bellows-balloon pneumatic circuit is at substantially zero ambient pressure so that any pressure that is generated from the pressurized cylinder 327 carrying the gas cannot accidentally overpressurize the balloon 119 which is in the patient.

This transfer of gas can be understood by examining the timing diagram which is shown in FIG. 11. As shown in FIG. 11 from top to bottom there is shown an ECG trace 331, a pump stroke trace 332, a V1 and V2 trace 333, an S1 trace 334, and a balloon pressure trace 336. A typical balloon inflation deflation cycle can last for approximately 2/5 (two fifths) seconds which would be equivalent to approximately 150 beats per minute, as for example, as a maximum down to approximately less than 1 cycle per second or less than 60 beats per minute. This cycle time is completely dependent on the ECG as represented by the trace 331. As shown by traces 332 and 333 at the beginning of the pump stroke, the solenoid operated valves V1 and V2 are pulsed for a period of time ranging from 10 to 20 milliseconds. This time is adjusted to provide the desired peak pressure in the solenoid pneumatic circuit. After closing of the solenoid operated valves V1 and V2, the solenoid S1 which is the solenoid assembly 291 is energized to cause movement of the piston 311 to compress the gas within the bellows balloon pneumatic circuit to create a pressure equivalent to approximately 60 millimeters of mercury to cause inflation of the balloon 119 as shown by the trace 336 when inflation of the balloon is desired.

At the time that deflation of the balloon 119 is desired, for example, at the peak 337 of the R-wave trace 331, the valves V1 and V2 are energized for a predetermined period of time ranging from 10 to 20 milliseconds to permit a slight amount of positive pressure within the pressurized balloon bellows pneumatic circuit to escape to ambient as indicated by the portion 339 of the trace 336, thereafter immediately deenergizing the solenoid V1 and permitting the spring 312 to return the piston 311 to its home position. This generates a negative pressure within the balloon-bellows balloon pneumatic circuit to approximately −30 millimeters of mercury in comparison to ambient. This negative pressure is held until the next inflation of the balloon 119 is desired. As soon as the next inflation of the balloon 119 is desired, the valves V1 and V2 are again pulsed to permit some of this negative pressure to escape as indicated by the portion 341 of the balloon pressure trace 336.

As soon as some of this negative pressure has been relieved, the solenoid S1 is again energized to create a positive pressure. This sequence is repeated continuously with a pulsation of the valves V1 and V2 stabilizing the generation of the positive and negative pressures over time. During this sequence of operation, the bellows balloon pneumatic circuit is flushed with the desired carbon dioxide or helium gas. This is accomplished by pulsation of the valve V2. During each cycle the valve V2 is pulsed for a short time to fill the linear plenum 324 with the desired gas. As this linear plenum 324 is filled with a volume of this gas from the container 327 any ambient air within the plenum 324 is exposed to ambient through the exhaust 325. At this point in time there is essentially zero pressure at the junction between the linear plenum 324 and the filter 322. During the time when there is negative pressure within the balloon bellows pneumatic circuit which is at the time that the piston 311 is being returned to its home position by the spring 312, zero pressure gas is transferred from the plenum 324 through the check valve 321 through the bellows balloon pneumatic circuit. At the end of the pneumatic cycle when there is high pressure in the balloon bellows circuit created by operation of the solenoid S1, a small amount of this pressurized gas which is a mixture of the beginning gas and the carbon dioxide or helium gas in the plenum 324 which has been mixed with an exit through the valve V1 and through the check valve 319 to ambient air.

It should be understood that when the gas inflation apparatus is placed in operation, the apparatus will begin with ambient air and with each stroke, additional carbon dioxide or helium gas supplied by the container 327 is introduced. After a number of cycles, a sufficiently high concentration of the desired gas, as for example, carbon dioxide or helium is attained in the balloon pneumatic circuit to be acceptable medically. The longer the gas inflation apparatus operates, the higher the percentage of the carbon dioxide gas or helium achieved within the bellows pneumatic circuitry until it eventually approaches approximately 100%. To initially facilitate flushing the ambient air with the desired gas, a temporary flush mode is provided by opening both V1 and V2 while cycling the solenoid S1 several times. This modality takes advantage of the full cycle time during which negative and positive pressures are generated in the bellows with respect to the exhaust and the gas input points for accelerating the exchange of resident air with the desired gas.

The stability of the balloon pressure over time is determined by the pulse width of the pulses on the valves V1 and V2. The valve V2 is pulsed at the same time as valve V1 because it is not critical when valve V2 is pulsed as long as some of the gas in the container 327 is transferred into the linear plenum 324. The timing of the operation of the valve V1 is important with the two cycles of operation of the valve V1 being labeled A and B with A being at the beginning of the stroke of the solenoid S1 and B being at the end of the stroke solenoid S1 which determines the long term stability of the pressures generated in the balloon. Thus if the length of the pulse time for the pulse A is increased, the pressure will increase in the balloon 119. Conversely if the time for the pulse A is decreased, the pressure in the balloon 119 will decrease. Similarly if the pulse time for the pulse B is increased the pressure in the balloon will decrease and if the width of pulse B is decreased, then the pressure in the balloon will increase. The reason for this is readily apparent. If a greater amount of negative pressure is exhausted then positive pressure, then over time the pressure will climb. Conversely, if a greater amount of positive pressure is exhausted than negative pressure, then over time the balloon pressure will fall. Thus it can be seen by adjusting the pulse width of the pulses A and B, the desired balloon pressure can be set and can be maintained over time.

Figure 12:
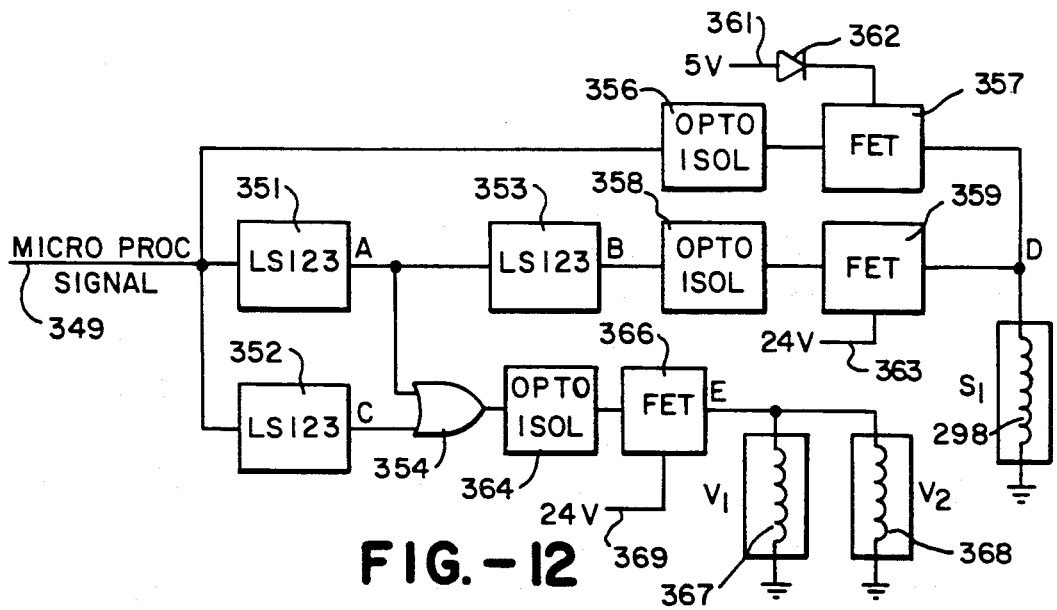
FIG. 12 is a block diagram of the electronic circuitry utilized for controlling the gas inflation apparatus shown in FIG. 10.
Figure 13:
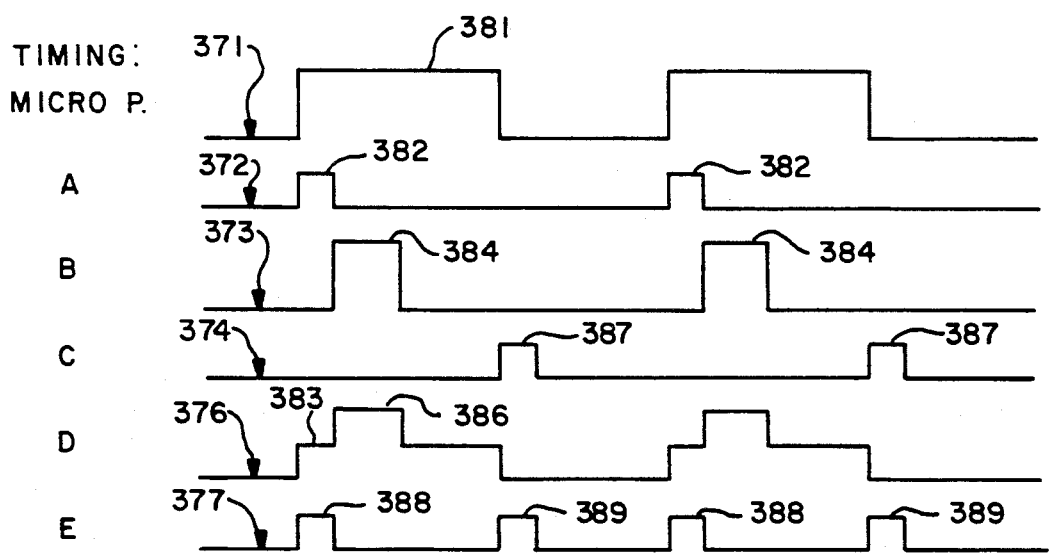
FIG. 13 is a chart showing the timing diagram for the circuitry shown in FIG. 12.

The circuitry which is utilized for operating the solenoid operated valves V1 and V2 and the solenoid S1 is shown in FIG. 12. The timing diagram for this circuit is shown in FIG. 13. As shown in FIG. 12, the circuitry consists of three one shot multi vibrators 351, 352 and 353 which can be of a conventional type as, for example, TTL circuitry such as the LS123 supplied by Texas Instruments. The output A of the multivibrator 351 is supplied to an OR gate 354 and also to the input of the multivibrator 353. The output 349 from the microprocessor 206 is supplied to the inputs of the two multivibrators 351 and 352. It is also supplied to an opto isolator 356 which has its output supplied to a field effect transistor 357 which has its output connected to the winding 298 of the solenoid S1. The output A of the multivibrator 351 is supplied to the input of the multivibrator 353 which has its output B supplied to another opto isolator 358 through a field effect transistor 359 to the winding 298 of the solenoid S1. The field effect transistor 357 is provided with a five volt supply 361 through a diode 362. The field effect transistor 359 is provided with a 24 volt supply 363. The output C of the multivibrator 352 is supplied to the OR gate 354 which is connected to an opto isolator 364. The opto isolator 364 is connected to a field effect transistor 366 to the windings 367 and 368 of the solenoid operated valves V1 and V2. As can be seen the other ends of the windings 298, 367 and 368 are connected to ground. The field effect transistor 366 is also provided with a 24 volt supply 369.

The output 349 for the microprocessor is indicated in the timing diagram in FIG. 13 as a curve 371. The curves at various points in the circuitry which are indicated as points A, B, C, D and E are shown as curves 372, 373, 374, 376 and 377 respectively.

The multivibrators 351, 352 and 353 are wired so that they are edge-triggered, that is, with either an up edge or a down edge providing a trigger to provide a pulse of the desired length. Thus when the microprocessor signal 349 supplies a pulse as shown by curve 371 and the edge of a pulse is ascertained by the multivibrator 351, its output A as indicated by the curve 372 provides a first pulse which is supplied through the OR gate 354 through the opto isolator 364 and the field effect transistor 366 to supply a voltage to the windings 367 and 368 to energize the valves V1 and V2. Thus it can be seen that the valves V1 and V2 are energized on the up edge of the pulse 381 from the microprocessor to provide a pulse 382 of desired length as, for example, from 10 to 20 microseconds for energizing the valves V1 and V2 as hereinbefore described.

At the same time as the up edge of the microprocessor pulse 381 occurs, a signal is supplied through the opto isolator FET to supply a five volt signal to the winding 298 of the solenoid S1. However, this voltage is not sufficient to actuate the solenoid S1 and therefore it will not be actuated with this voltage. This voltage is indicated by the step 383 in the curve 376.

The output from the multivibrator 351 is also supplied to the multivibrator 353 which is triggered on the negative going edge of the pulse 382 to provide the pulse 384 in the curve 373 from the output B of the multivibrator 353. This pulse 384 is of a suitable width as, for example, 50 milliseconds which is supplied through the opto isolator 358 and the FET 359 to supply 24 volts to the winding 298 of the solenoid S1 which will cause energization of the solenoid S1 to cause it to operate to advance the piston 311 in the manner hereinbefore described. This pulse 384 has a suitable width as, for example, 50 milliseconds. The 24 volts which is supplied to the winding 298 of the solenoid S1 is represented by the step 386 in curve 376.

The third multivibrator 352 is triggered by the negative going edge of the pulse 381 of the microprocessor signal and its output C as shown by the curve 374 produces a pulse 387 having a suitable width as, for example, 10 to 20 milliseconds to supply a signal through the OR gate 354 through the opto oscillator 364, the FET 366 to the windings 367 and 368 of the valves V1 and V2. The output E from the FET 366 is shown by the curve 377 in which the pulses 388 correspond to the pulses 382 and the pulses 389 correspond to the pulses 387.

From the foregoing it can be seen that the solenoid S1 is operated to move the full amount of its travel during the 50 millisecond pulse 384. At the end of the 50 milliseconds, the voltage on the solenoid drops down to 5 volts which is sufficient to hold the solenoid in place for the duration of the cycle as indicated by the pulses 381 of the microprocessor.

Figure 14:
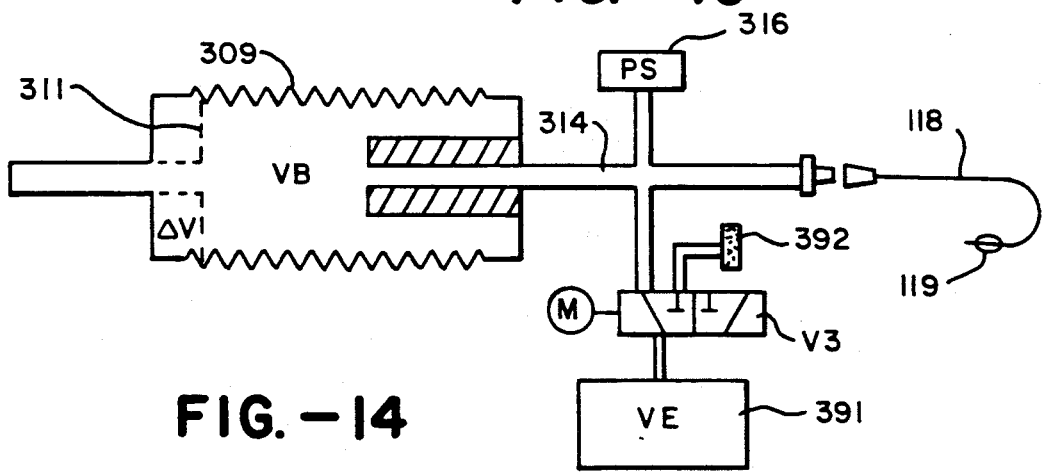
FIG. 14 is a schematic diagram of an alternative air inflation mechanism for the balloon.

In FIG. 14, there is shown another embodiment of a pneumatic circuit which can be utilized for creating a balloon pressure without the use of a pressurized gas, as for example, from the container 327 as in connection with the embodiment previously described. As shown in FIG. 14, this gas inflation apparatus utilizes the same bellows 309 with the piston 311 to supply air to an output tube 314 which is connected to the catheter 118 and the balloon 119. The pressure transducer 316 is also provided. The tubing 314 is connected to a solenoid operated valve V3 which is similar to the solenoid operated valve V1 or V2 as hereinbefore described with the exception that it is a three-way solenoid operated valve rather than a two-way solenoid operated valve. The valve V3 is connected to an extra plenum chamber 391 upon energization of the solenoid S1, a certain positive pressure of gas is generated of approximately 60 millimeters of mercury which pressure is created in the balloon 119 as well as in the extra plenum chamber 391 through the open valve V3. Upon completion of the upstroke of the piston 311, the solenoid V3 is closed to isolate the pressurized volume VE in the extra plenum 391. The pressurized gas in the extra plenum 91 is then permitted to escape to ambient through the valve V3 through the filtered exhaust 392. The volume VB in the bellows as well as in the balloon is at this point isolated from the extra plenum chamber 391. Upon the reverse stroke of the solenoid S1 and the movement of the piston 311, a negative pressure is created because the volume VE in the extra plenum 391 has been isolated from the bellows balloon pneumatic circuit. Once this negative pressure has been generated following the first upstroke, upon each downstroke cycle the negative pressure will again be created because of the volume of gas which has been removed by the isolated extra plenum 391. Assuming there are no leaks in the system, operation of the apparatus can be sensed by the pressure transducer 316 and a signal is supplied to the microprocessor which supplies a signal to the solenoid operated valve V3 to connect the plenum 391 to the tubing 314 to remove gas from the bellows balloon pneumatic circuitry and then closing the solenoid operated valve V3 to isolate the extra plenum 391 from the bellows pneumatic circuitry at the end of the upstroke.

After this initialization, the appropriate positive-negative pressures can be maintained within desired limits. As explained previously, if this initialization is not maintained, the apparatus can be reinitialized. Thus by switching the extra plenum 391 into and out of the pneumatic circuitry, it is possible to generate the desired negative and positive pressures. By switching the extra plenum 391 into and out of the pneumatic circuitry, it is possible to generate a specific negative pressure from the specific stroke of the solenoid and the bellows-balloon pneumatic circuitry.

If it is desired to generate additional negative pressure the size of the extra plenum can be increased or alternatively, the apparatus can be cycled additional times, as for example, two or three times in succession to obtain the desired negative pressure. By cycling the extra plenum into and out of the pneumatic circuitry, it is possible to change the positive and negative destination pressures within the bellows balloon pneumatic circuitry. The balloon pressure generation apparatus shown in FIG. 14 makes it possible to inflate and deflate the balloon 119 when filtered air is adequate. The pneumatic circuitry permits the generation of the desired positive and negative pressures without the use of a vacuum pump and without relying upon the use of pressurized gasses.

It has been found that the pneumatic systems utilized for inflating and deflating the balloons in a positive and negative manner is advantageous over the use of an auto-inflatable balloon hereinbefore described. It does not require a specific volume of blood to be used each time of balloon inflation. By way of example, utilizing the auto-inflatable balloon and assuming the balloon has a volume of one-half of a cubic centimeter on an 8 or 10 millimeter balloon at 120 beats per minute uses 60 cubic centimeters of blood during each minute for inflating and deflating the balloon. This volume of blood travels to and from the disposable pump and in the balloon catheter during each cycle instead of going out the tip and being utilized as flow for retroperfusion. Utilizing a gas as the inflation medium for the balloon, this volume of blood which was previously used for balloon inflation and deflation can now be passed out of the tip of the catheter and increase the flow for retroperfusion. Alternatively, the pumping pressure or the cycling of the pump can be decreased.

It also has been found that the auto-inflatable balloon is sometimes undesirable because it is possible for the pressure of the blood in the coronary sinus to backfill the balloon through the tip valve and to cause undesirable high pressures in the coronary sinus. With the gas inflation system for the balloon, this cannot occur because the balloon is independently controlled and inflated and deflated. Also it is held deflated in a positive manner so that there cannot be an accidental buildup of coronary sinus pressure.

An additional safety factor over an auto-inflatable balloon is provided by the fact that the coronary sinus pressure does not increase beyond the balloon inflation pressure of approximately 60 millimeters of mercury. Should conditions exist to generate a greater pressure, the balloon will automatically decrease in size to allow this greater coronary sinus pressure to decrease and equilibrate with the balloon pressure even without active deflation of the balloon with the microprocessor.

Figure 15:
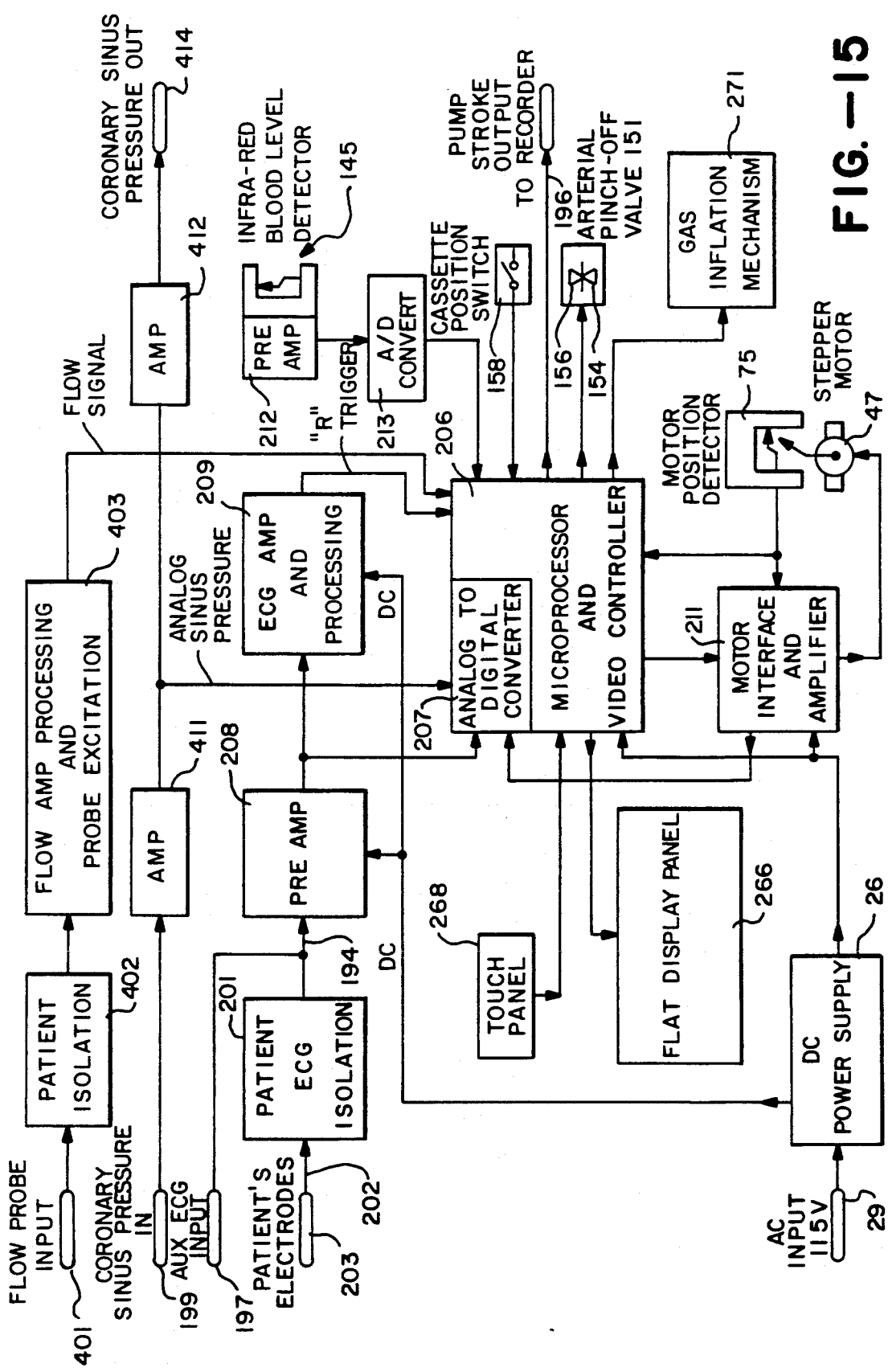
FIG. 15 is a block diagram of the electronic circuitry for controlling the apparatus shown in FIGS. 8 and 9.

The circuitry which is shown in FIG. 6 for the previous embodiment has been slightly revised as shown in the circuitry shown in FIG. 15. The keyboard 171 has been eliminated as has the heart rate display 181 and the flow display 182 which have been replaced by the touch panel 268 and the flat panel display 266.

An integral blood flow meter has been incorporated into the console 12 which can be of a conventional type and is provided with a probe 401 which is connected to patient isolation circuitry 402 to a flow amplifier processing and probe exitation circuitry 403 to provide a flow signal to the microprocessor 206.

In addition, a pressure transducer output from a coronary sinus pressure transducer 406 (see FIG. 1) of a conventional type is supplied to the cable 199 on the console 12. It can be identified as "coronary sinus pressure in". The transducer 406 is connected by tubing 407 to a y fitting 408 connected to a three lumen catheter 118a. The cable 199 is connected to an amplifier 411 which supplies an analog sinus pressure indication to the analog digital converter 207 to the microprocessor controller 206. This makes it possible to utilize sinus pressure to automatically control the blood pumping and/or balloon inflation period. The output from the amplifier 411 is also supplied to another amplifier 412 to an output terminal 413 to a cable 414 which can be identified as "coronary sinus out".

A patient ECG apparatus 201 has been incorporated into the console 12 so that a direct isolation amplified connection can be made to the patient through the patient electrodes 203. The cable 202 in FIG. 8 is used for making direct contact to electrodes 203 placed on the patient and can be identified as "ECG in". The auxiliary ECG input 191 has been retained in the event it is desired to utilize n external ECG monitor and is identified as "AUX ECG input".

As also can be seen the gas inflation mechanism 271 has its input connected to the output of the microprocessor 206 for the purposes hereinbefore described.

The cable 197 is adapted to be connected to the auxiliary ECG and can be identified as "AUX ECG in". Conduit 198 is connected to the pump and can be identified as "Pump Stroke". Conduit 198 is connected to the tubing 314. The tubing 314 is also connected to a fitting 416 mounted on a side wall of the console 12. An extension tube 417 connects to the fitting 416 to another y fitting 418 connected to the three lumen catheter 118a.

The operation of the system and apparatus for retroperfusion is readily apparent from the description hereinbefore given with respect to the previous embodiment. The use of the apparatus for retroinfusion may now be briefly described as follows. Let it be assumed that a typical drug such as streptokinase is to delivered systemically and it is desirable to reduce the amount of the drug delivered to the patient. By delivering the same directly to the heart via the coronary sinus it is possible to achieve the same positive coronary effect while utilizing less volume of the drug and therefore decreasing the systemic side effects. This can be readily accomplished with the present apparatus by introducing the drug into the container 276 and having the same delivered directly to the coronary sinus during each pump cycle. By way of example, the balloon can be inflated and held inflated during the time that the diluted drug is being pumped continuously or nearly continuously into the coronary sinus until the coronary sinus reaches a certain limit at which time the balloon can be deflated and the pumping of the drug terminated.

It is apparent from the foregoing that there has been provided a retroperfusion and retroinfusion system, apparatus and method which has many advantages. The use of the gas inflation mechanism makes it possible to positively inflate and deflate the balloon within very precise limits. It is possible to introduce drugs into the coronary sinus with great efficacy eliminating the necessity of introducing excess amounts of the drug to obtain the desired effect without associated systemic side effects.

What is claimed is:

1. Apparatus for supplying arterial blood from an artery of a patient to a vein of the same patient forming a part of the venous side of the patient's heart, a catheter having a proximal and a distal extremity an inflatable balloon carried by the distal extremity, the catheter including a balloon inflation lumen in communication with the balloon, means connecting the proximal extremity of the catheter to the artery of the patient, means connecting the distal extremity of the catheter to the vein of the patient, blood pump means connected into the catheter for pumping blood from the proximal extremity of the catheter to the distal extremity of the catheter, motorized means for cyclically operating the blood pump means, gas pressure generation means the balloon inflation lumen and control means connected to the motorized means for operating the blood pump, said control means including means for establishing an R to R interval for the patient's heart assuming a steady heart beat and for timing the cyclical operation of the blood pump means in accordance with the R to R interval and means connecting the control means to the gas generation means for synchronizing the inflation and deflation of the balloon with the cyclic operation of the pump.

2. A control apparatus for supplying arterial blood of a patient to the venous side of a patient's heart by the use of a catheter having a distal extremity, an inflatable balloon carried by the distal extremity and having a balloon inflation lumen in communication with the balloon control apparatus comprising, a blood pump having an inlet adapted to be connected to a blood vessel of the patient and having an outlet adapted to be connected to another blood vessel of the patient for pumping the blood of the patient, motorized means for operating the blood pump and gas pressure generation means adapted to be connected to the lumen in communication with the balloon of the catheter and synchronized with the operation of the blood pump for inflating and deflating the balloon with a gas, the gas pressure generation means including a chamber, a piston movably mounted within said chamber, said chamber having an outlet, means for operating the piston, valve operated means connected to the output of the chamber and adapted to be connected to the balloon inflation lumen, said valve operated means including means for ensuring that the balloon is inflated with a predetermined positive pressure and deflated with a predetermined negative pressure with each stroke of the piston.

3. Apparatus as in claim 2 together with a supply of gas connected to the valve operated means.

4. Apparatus as in claim 3 further comprising a solenoid coupled to said valve means for operating said valve means.

5. Apparatus as in claim 2 together with a plenum chamber connected to the valve means.

6. Apparatus as in claim 5 wherein the plenum chamber is open to the atmosphere.

7. Apparatus as in claim 5 wherein the plenum chamber is a closed chamber.

8. A control apparatus for supplying arterial blood of a patient to the venous side of a patient's heart by the use of a catheter having a distal extremity, an inflatable balloon carried by the distal extremity and having a balloon inflation lumen in communication with the balloon, the control apparatus comprising a blood pump having an inlet adapted to be connected to a blood vessel of the patient and having an outlet adapted to be connected to another blood vessel of the patient for pumping the blood of the patient, motorized means for operating the blood pump and gas pressure generation means adapted to be connected to the lumen in communication with the balloon of the catheter and synchronized with the operation of the blood pump for inflating and deflating the balloon with a gas, the gas pressure generation means including a chamber, a piston movably mounted within said chamber, said chamber having an outlet, means for operating the piston, valve operated means connected to the output of the chamber and adapted to be connected to the balloon inflation lumen, said valve operated means including means for ensuring that the balloon is inflated with a predetermined positive pressure and deflated with a predetermined negative pressure with each stroke of the piston, said chamber being in the form of a collapsible bellows, said piston being a reciprocable piston, said means for operating said piston including a solenoid for moving the piston in one direction and spring means for moving the piston in an opposite direction.

9. Apparatus as in claim 8 wherein the supply of gas is in a closed container.

10. Apparatus as in claim 8 together with a supply of gas having substantially zero pressure, and means for connecting the supply of gas to the chamber of the gas pump.

11. Apparatus as in claim 8 together with means for supplying ambient air to said chamber.

12. A method for supplying arterial blood into a venous region of the heart by the use of a catheter having a distal extremity, an inflatable balloon carried by the distal extremity, a balloon inflation lumen in communication with the balloon and having a blood flow lumen therein through which the blood can flow, the method comprising the steps of establishing an R to R interval for the patient's heart assuming a steady heart beat, cyclically supplying arterial blood from the patient under positive pressure through the blood flow lumen of the catheter into a venous region of the heart in accordance with the established R to R interval and periodically inflating the balloon with a gas in synchronism with the supplying of arterial blood of the patient into the catheter.

13. A method as in claim 12 together with the step of skipping at least a portion of a cycle in the event a very irregular heart beat of the patient occurs.

14. In a method for supplying arterial blood into a venous region of the heart by the use of a catheter having a distal extremity, an inflatable balloon carried by the distal extremity, a balloon inflation lumen in communication with the balloon and having a blood flow lumen therein through which the blood can flow, the method comprising the steps of supplying arterial blood from the patient under positive pressure through the blood flow lumen of the catheter at predetermined periods of time into a venous region of the heart and periodically inflating the balloon with a gas in synchronism with the supplying of arterial blood of the patient into the catheter, and ensuring that the balloon is inflated with a predetermined positive pressure and is deflated under a predetermined negative pressure.

15. A method for supplying arterial blood into a venous region of the heart by the use of a catheter having a distal extremity, an inflatable balloon carried by the distal extremity, a balloon inflation lumen in communication with the balloon and having a blood flow lumen therein through which the blood can flow, the method comprising the steps of supplying arterial blood from the patient under positive pressure through the blood flow lumen of the catheter at predetermined periods of time into a venous region of the heart and periodically inflating the balloon with a gas in synchronism with the supplying of arterial blood of the patient into the catheter and supplying additional gas when needed for inflating the balloon after the initial inflation of the balloon.

16. A method for supplying arterial blood into a venous region of the heart of a patient by the use of a catheter having a distal extremity, an inflatable balloon carried by the distal extremity, a balloon inflation lumen in communication with the balloon and having a blood flow lumen therein through which the blood can flow, the method comprising the steps of establishing an R to R interval for the patient's heart assuming a steady heart beat, cyclically supplying arterial blood from the patient under positive pressure through the blood flow lumen of the catheter in a cyclical manner in accordance with the established R to R interval into a venous region of the heart and periodically inflating the balloon with a gas in synchronism with the supplying of arterial blood of the patient into the catheter and supplying a diluent to the arterial blood as it is drawn from the patient so that retroinfusion of the diluent occurs.

* * * * *